United States Patent
Contorni et al.

(10) Patent No.: US 10,568,953 B2
(45) Date of Patent: Feb. 25, 2020

(54) ADJUVANTING MENINGOCOCCAL FACTOR H BINDING PROTEIN

(71) Applicant: GlaxoSmithKline Biologicals SA, Rixensart (BE)

(72) Inventors: Mario Contorni, Siena (IT); Lorenzo Tarli, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 16/269,370

(22) Filed: Feb. 6, 2019

(65) Prior Publication Data

US 2019/0151430 A1    May 23, 2019

Related U.S. Application Data

(60) Continuation of application No. 15/604,054, filed on May 24, 2017, now Pat. No. 10,245,311, which is a continuation of application No. 15/393,092, filed on Dec. 28, 2016, now abandoned, which is a division of application No. 14/307,001, filed on Jun. 17, 2014, now Pat. No. 9,572,884, which is a continuation of application No. 13/767,853, filed on Feb. 14, 2013, now Pat. No. 8,834,888, which is a continuation of application No. 13/403,865, filed on Feb. 23, 2012, now Pat. No. 8,398,988, which is a continuation of application No. 13/260,534, filed as application No. PCT/IB2010/000733 on Mar. 24, 2010, now abandoned.

(60) Provisional application No. 61/162,999, filed on Mar. 24, 2009.

(51) Int. Cl.
| | |
|---|---|
| A61K 39/395 | (2006.01) |
| A61K 39/095 | (2006.01) |
| A61K 47/02 | (2006.01) |
| A61K 39/00 | (2006.01) |

(52) U.S. Cl.
CPC ............ *A61K 39/095* (2013.01); *A61K 47/02* (2013.01); *A61K 2039/55505* (2013.01); *A61K 2039/55583* (2013.01); *A61K 2039/6018* (2013.01); *A61K 2039/70* (2013.01)

(58) Field of Classification Search
CPC .................................................. A61K 39/095
See application file for complete search history.

(56) References Cited

U.S. PATENT DOCUMENTS

| | | | |
|---|---|---|---|
| 7,348,006 B2 | 3/2008 | Contorni et al. |
| 7,576,176 B1 | 8/2009 | Fraser et al. |
| 7,785,608 B2 | 8/2010 | Zlotnick et al. |
| 7,862,827 B2 | 1/2011 | Giuliani et al. |
| 8,101,194 B2 | 1/2012 | Zlotnick et al. |
| 8,226,960 B2 | 7/2012 | Masignani et al. |
| 8,273,360 B2 | 9/2012 | Pizza et al. |
| 8,293,251 B2 | 10/2012 | Scarlato et al. |
| 8,394,390 B2 | 3/2013 | Galeotti et al. |
| 8,398,988 B2 | 3/2013 | Contorni et al. |
| 8,398,999 B2 | 3/2013 | Masignani et al. |
| 8,470,340 B2 | 6/2013 | Beernink et al. |
| 8,524,251 B2 | 9/2013 | Fraser et al. |
| 8,563,007 B1 | 10/2013 | Zlotnick et al. |
| 8,574,597 B2 | 11/2013 | Zlotnick |
| 8,663,656 B2 | 3/2014 | Pizza |
| 8,734,812 B1 | 5/2014 | Galeotti et al. |
| 8,765,135 B2 | 7/2014 | Contorni |
| 8,834,888 B2 | 9/2014 | Contorni et al. |
| 8,840,907 B2 | 9/2014 | Pizza |
| 8,968,748 B2 | 3/2015 | Granoff et al. |
| 8,980,277 B2 | 3/2015 | Pizza |
| 8,980,286 B2 | 3/2015 | Comanducci |
| 9,011,869 B2 | 4/2015 | Pizza |
| 9,056,075 B2 | 6/2015 | Pizza |
| 9,067,987 B2 | 6/2015 | Galeotti et al. |
| 9,150,898 B2 | 10/2015 | Arico |

(Continued)

FOREIGN PATENT DOCUMENTS

| | | |
|---|---|---|
| EP | 0467714 A1 | 1/1992 |
| EP | 1534326 A2 | 6/2005 |

(Continued)

OTHER PUBLICATIONS 1997-11-17-NM_shotgun.dbs and 1997-12-15-NM.dbs, located at <ftp://ftp.sanger.ac.uk/pub/pathogens/nm/old data/> Generated Jul. 23, 2008. 2 pages.

(Continued)

*Primary Examiner* — Albert M Navarro
(74) *Attorney, Agent, or Firm* — Morrison & Foerster, LLP

(57) ABSTRACT

Factor H binding protein (fHBP) has been proposed for use in immunising against serogroup B meningococcus ('MenB'). This antigen can be efficiently adsorbed to an aluminium hydroxyphosphate adjuvant by (i) ensuring that adsorption takes place at a pH which is equal to or below the adjuvant's point of zero charge (PZC), and/or (ii) selecting a fHBP and adjuvant with an isoelectric point/PZC within the range of 5.0 to 7, and/or (iii) selecting a fHBP with an isoelectric point above the adjuvant's PZC and using a buffer to bring the pH to within 1.2 pH units of the PZC. The adsorption is particularly useful for compositions which include multiple fHBP variants, and also in situations where an aluminium hydroxide adjuvant should be avoided. Buffered pharmaceutical compositions can include at least two different meningococcal fHBP antigens, both of which are at least 85% adsorbed to aluminium hydroxyphosphate adjuvant.

20 Claims, No Drawings
Specification includes a Sequence Listing.

(56) References Cited

U.S. PATENT DOCUMENTS

| | | | |
|---|---|---|---|
| 9,156,894 | B2 | 10/2015 | Masignani et al. |
| 9,249,196 | B2 | 2/2016 | Fraser et al. |
| 9,364,528 | B1 | 6/2016 | Giuliani et al. |
| 9,468,673 | B2 | 10/2016 | Pizza |
| 9,526,776 | B2 | 12/2016 | Baudner |
| 9,610,342 | B2 | 4/2017 | Giuliani |
| 2003/0035806 | A1 | 2/2003 | D'Ambra et al. |
| 2004/0092711 | A1 | 5/2004 | Arico |
| 2004/0110670 | A1 | 6/2004 | Arico et al. |
| 2004/0167068 | A1 | 8/2004 | Zlotnick et al. |
| 2006/0008476 | A1 | 1/2006 | Pizza et al. |
| 2006/0051840 | A1 | 3/2006 | Arico et al. |
| 2006/0171957 | A1 | 8/2006 | Pizza |
| 2006/0240045 | A1 | 10/2006 | Berthet et al. |
| 2006/0251670 | A1 | 11/2006 | Comanducci et al. |
| 2007/0026021 | A1 | 2/2007 | Fraser et al. |
| 2007/0082014 | A1 | 4/2007 | Costantino |
| 2007/0253984 | A1 | 11/2007 | Khandke et al. |
| 2008/0248065 | A1 | 10/2008 | Granoff et al. |
| 2009/0035328 | A1 | 2/2009 | Granoff |
| 2009/0285845 | A1 | 11/2009 | Masignani et al. |
| 2010/0267931 | A1 | 10/2010 | Arico et al. |
| 2011/0020390 | A1 | 1/2011 | Pizza et al. |
| 2012/0070458 | A1 | 3/2012 | Contorni et al. |
| 2012/0107339 | A1 | 5/2012 | Granoff et al. |
| 2014/0037668 | A1 | 2/2014 | Giuliani et al. |
| 2014/0363462 | A1 | 12/2014 | Arico et al. |
| 2015/0079124 | A1 | 3/2015 | Fraser et al. |
| 2015/0086582 | A1 | 3/2015 | Fraser et al. |

FOREIGN PATENT DOCUMENTS

| | | |
|---|---|---|
| EP | 1645631 B1 | 10/2007 |
| EP | 2351767 A2 | 8/2011 |
| EP | 1790660 B1 | 6/2012 |
| WO | WO96/29412 A1 | 9/1996 |
| WO | WO98/17805 A2 | 4/1998 |
| WO | WO98/18930 A2 | 5/1998 |
| WO | WO99/57280 A2 | 11/1999 |
| WO | WO2000/022430 A2 | 4/2000 |
| WO | WO2000/066791 A1 | 11/2000 |
| WO | WO2001/031019 A2 | 5/2001 |
| WO | WO2001/052885 A1 | 7/2001 |
| WO | WO2001/064920 A2 | 9/2001 |
| WO | WO2001/064922 A2 | 9/2001 |
| WO | WO2003/009869 A1 | 2/2003 |
| WO | WO2003/020756 A2 | 3/2003 |
| WO | WO2003/063766 A2 | 8/2003 |
| WO | WO2004/032958 A1 | 4/2004 |
| WO | WO2004/048404 A2 | 6/2004 |
| WO | WO2004/065603 A2 | 8/2004 |
| WO | WO2004/094596 A2 | 11/2004 |
| WO | WO2005/102384 A2 | 11/2005 |
| WO | WO2006/024954 A2 | 3/2006 |
| WO | WO2006/081259 A2 | 8/2006 |
| WO | WO2007/060548 A2 | 5/2007 |
| WO | WO2007/127665 A2 | 11/2007 |
| WO | WO2008/079372 A2 | 7/2008 |
| WO | WO2008/125985 A2 | 10/2008 |
| WO | WO2008/149238 A2 | 12/2008 |
| WO | WO2009/038889 A1 | 3/2009 |
| WO | WO2009/104097 A2 | 8/2009 |
| WO | WO2010/028859 A1 | 3/2010 |
| WO | WO2010/046715 A1 | 4/2010 |
| WO | WO2011/051893 A1 | 5/2011 |
| WO | WO2011/110634 A1 | 9/2011 |
| WO | WO2011/126863 A1 | 10/2011 |
| WO | WO2012/032489 A1 | 3/2012 |
| WO | WO2013/177397 A1 | 11/2013 |

OTHER PUBLICATIONS

Adams (1996). "Should Non-Peer-Reviewed Raw DNA Sequence Data Release Be Forced on the Scientific Community?," Science, 274: 534-536.

Aderson et al. (2010). "Effectiveness of a bivalent factor H binding protein vaccine across Neisseria meningitidis serogroups," 17th International Pathogenic Neisseria Conference 2010, p. 196.

Ala'Aldeen et al. (2010) "Human antibody response to the meningococcal factor H binding protein (LP2086) during invasive disease, colonization and carriage," Vaccine 28:7667-75.

Alignment of Seq ID No. 19 of EP2327719 against Seq ID Nos. 92, 94, 96, 98, 100, 102, 104, 106, and 108 of WO/2003/063766, filed in opposition against EP2327719, submitted May 20, 2015, 9 pages.

Alignment of Seq ID No. 42 of EP2258716 against Seq ID No. 41 of EP2258716, filed in opposition against EP2258716, submitted Apr. 16, 2015, 1 page.

Alignment of Seq ID No. 42 of EP2258716 against Seq ID Nos. 50, 52, 54, 56, 58, 60, 62, 64, 66, 68, 70, and 72 of WO/2003/063766, filed in opposition against EP2258716, submitted Apr. 16, 2015, 12 pages.

Alignment of Seq ID No. 42 of EP2258716 with NMA0586, submitted Jul. 29, 2016, filed in opposition against EP2258716, 1 page.

Alignment of the sequence of strain Z2491 with sequences coding for subfamily A 2086 proteins disclosed by WO 2003/063766, filed in opposition against EP1562983 on Sep. 13, 2016, 36 pages.

Alignments of Seq ID Nos. 42-44 of WO2004048404 with Seq ID No. 24, 33 and 41 of WO2004048404, filed in relation to EP1562983, submitted Mar. 14, 2017 , 5 pages.

Ambrose et al. (2006). "Characterization of LP2086 expression in Neisseria meningitidis," 15th International Pathogenic Neisseria Conference 2006, p. 103.

Amended Defense and Counterclaim, Appendix II, UK High Court proceedings in *GlaxoSmithKline UK Limited* v. *Wyeth Holdings LLC*, dated Aug. 10, 2015, filed in opposition against EP2258716, 45 pages.

Amended Defense and Counterclaim, Jul. 24, 2015, Claim No. HP-2015-000022, *Glaxosmithkline UK LTD* v. *Wyeth Holdings LLC*, 4 pages.

Anderson et al. (2008). "Functional cross-reactive antibodies are elicited by a group B Neisseria meningitidis bivalent recombinant lipidated LP2086 vaccine in cynomolgusmacaques," 16th International Pathogenic Neisseria Conference (IPNC) P100, pp. 170-171.

Anderson et al. (2009). "Development of a factor H binding protein vaccine for broad protection against invasive Neisseria meningitidis serogroup B (MnB) disease," 10th European Meningococcal Disease Society Congress 2009, p. 39.

Anderson et al. (2009). "Epidemiology of the serogroup B Neisseria meningitidis (MnB) factor H binding protein and implications for vaccine development," European Society for Paediatric Infectious Disease Symposium 2009, p. 505.

Anderson et al. (2012). "Potential impact of the bivalent rLP2086 vaccine on Neisseria meningitidis invasive disease and carriage isolates in two adolescent populations," European Society for Paediatric Infectious Disease Symposium 2012, p. 807.

Anderson et al. (2013) "Potential impact of the bivalent rLP2086 vaccine on Neisseria meningitidis carriage and invasive serogroup B disease," Hum Vacc Immunotherap 9:471-9.

Annex 1 to the Amended Defence and Counterclaim, Jun. 24, 2015, Claim No. HP-2015-000022, *Glaxosmithkline UK LTD* v. *Wyeth Holdings LLC*, 40 pages.

Appendix A, comparison of genes predicted within "contig295" by ORFFinder, filed in relation to EP1645631 on Aug. 15, 2016, 1 page.

Appendix I to Statement of Grounds of Appeal filed by df-mp on Sep. 28, 2012, in relation to EP1645631, 1 page.

Appendix II to Statement of Grounds of Appeal filed by df-mp on Sep. 28, 2012, in relation to EP1645631, 2 pages.

Approved Judgment, dated May 12, 2016, UK High Court Decision in *GlaxoSmithKline UK Limited* v. *Wyeth Holdings LLC*, filed in opposition against EP2258716 and EP1562983, 66 pages.

Bai et al. (2011) "Recombinant protein meningococcal serogroup B vaccine combined with outer membrane vesicles." Expert Opin Biol Ther. 11:969-85.

(56) References Cited

OTHER PUBLICATIONS

Beernink (Jul. 2010) "Impaired immunogenicity of a meningococcal factor H-binding protein vaccine engineered to eliminate factor h binding," Clin Vac Immunol 17(7):1074-1078.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.
Beernink et al. (2009) "Meningococcal factor H-binding protein variants expressed by epidemic capsular group A, W-135, and X strains from Africa." J Infect Dis 199:1360-8.
Beernink et al. (2011). "A meningococcal factor H binding protein mutant that eliminates factor H binding enhances protective antibody responses to vaccination," J Immunol, 186(6):3606-14.
Beernink et al. (Jun. 2008). "Bactericidal antibody responses, induced by meningococcal recombinant chimeric factor H-binding protein vaccines," Infection and Immunity 76(6):2568-2575.
Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.
BenMohamed et al. (2002). "Lipopeptide vaccines—yesterday, today, and tomorrow," Lancet 2(7):425-431.
Bentley et al. (2004). Identification of two immunologically distinct domains on the LP2086 outer membrane lipoprotein of Neisseria meningitidis, 14th International Pathogenic Neisseria Conference 2004, p. 144.
Bernfield et al. (2002). "Identification of a novel vaccine candidate for group B Neisseria meningitidis," 13th International Pathogenic Neisseria Conference 2002, Poster, 20 pages.
Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, p. 116.
Biswas et al. (1995). "Characterization of IbpA, the structural gene for a lactoferrin receptor in Neisseria gonorrhoeae," Infection and Immunity, 63(8): 2958-2967.
Blattner et al. (1997). "The complete genome sequence of *Escherichia coli* K-12," Science 277 (5331): 1453-1474.
Bos et al. (2014), "Involvement of *Neisseria meningitidis* Lipoprotein GNA2091 in the Assembly of a Subset of Outer Membrane Protein," J. Biol. Chem 289(22):15602-610.
Boslego et al. (1991). "Gonorrhea Vaccines," Chapter 17 in *Vaccines and Immunotherapy*, Cryz S.J. (Ed.), Pergamon Press: New York, NY, pp. 211-223.
Bouvier et al. (1991). "A gene for a new lipoprotein in the dapA-purC interval of the *Escherichia coli* chromosome," J Bacteriol 173(17):5523-5531.
Brendish and Read. (2015). "Neisseria meningitidis serogroup B bivalent factor H binding protein vaccine," Expert Rev. Vaccines, 14(4):493-503.
Cannon (1989). "Conserved Lipoproteins of Pathogenic Neisseria Species Bearing the H.8 Epitope: Lipid-Modified Azurin and H.8 Outer Membrane Protein," Clinical Microbiology Reviews 2(Suppl.):S1-S4.
Cantini et al. (Mar. 2006). "Solution Structure of the Immunodominant Domain of Protective Antigen GNA 1870 of Neisseria meningitidis," *Journal of Biological Chemistry* 281(11): 7220-7227.
CECMED (Dec. 2, 2011), "Resumen de las Caracteristicas del Producto: VA-MENGOC-BC," Ministerio de Salud Publica de Cuba, 4 pages. (3 page English translation included).
Chen, et al. (1994). "Determination of the optimal aligned spacing between the Shine-Dalgarno sequence and the translation initiation codon of *Escherichia coli* mRNAs," Nucleic Acids Res. 22(23):4953-4957.
Claimant's Notice of Experiments, UK High Court proceedings in *GlaxoSmithKline UK Limited* v. *Wyeth Holdings LLC*, submitted Jul. 28, 2016 in opposition proceedings against EP2258716 and EP1562983, 8 pages.
Claimant's Amended Grounds of Invalidity under CPR 17.1 (2)(a) on Jul. 16, 2015, in respect of European Patent (UK) No. 2,343,308. In the High Court of Justice Chancery Division Patents Court, between GlaxoSmithKline UK Limited and Wyeth Holdings LLC. 9 pages.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1> 3 pages.
Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028&rank=1> 4 pages.
Clustal alignment of menA and menB sequences with upstream sequence, performed using Clustal on Genbank NC_003116.1 and NC_003112.2, Submitted in opposition proceedings of EP1645631 on Sep. 28, 2012. 2 pages.
Cohn et al. (2010). "Potential Impact of Serogroup B Vaccines: Prevalence of candidate vaccine antigens among invasive Neisseria meningitidis isolates in the United States," 17th International Pathogenic Neisseria Conference 2010, p. 77.
Cole et al. (1998). "Deciphering the biology of *Mycobacterium* tuberculosis from the complete genome sequence," Nature 394:651-653.
Communication from the Examining Division, filed in Opposition against EP2975127, dated Mar. 24, 2017, 4 pages.
Compton (1990). "Degenerate primers for DNA amplification," in "PCR Protocols: A Guide to Methods and Applications," Innis et al. (Eds.), pp. 39-45, Academic Press, San diego.
Contig 295 from Sanger nm 'old data' ORF Finder, filed in relation to EP1645631, dated Jul. 1, 2013, 9 pages.
Contig 295 ORF Finder, filed in relation to EP1645631, dated Sep. 21, 2012, 2 pages.
Cordis, "Preparation of meningococcal antigens," posted online on Feb. 2, 2005, 2 pages.
Cruse et al. (2003). Illustrated Dictionary of Immunology, $2^{nd}$ Ed. CRC Press, pp. 46, 166, and 382.
Database accession No. NMB1994 (cf. XP2231040) (Tettelin et al.), uploaded Oct. 1, 2000. 337 pages.
Database UniProt ( Feb. 6, 2007). Submitted name: Putative lipoprotein, Uniprot accession No. A11Q30, PIR No. G81977, retrieved Jan. 20, 2016 from <http://www.uniprot.org/uniprot/A11Q30>, 7 pages.
Database UniProt (Oct. 1, 2000), "SubName: Full=Uncharacterized protein" retrieved from EBI, accession No. Q9JXV4 Database accession No. Q9JXV4, PIR No. D81032, 2 pages.
De Moraes JC, et al. (1992). Protective efficacy of a serogroup B meningococcal vaccine in Sao Paulo, Brazil. Lancet 340: 1074-1078.
Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).
Decision in Opposition Proceedings, Filed in opposition against EP1645631, Dated May 30, 2017, 3 pages.
Decision of Technical Board of Appeal for EP942983, dated Nov. 14, 2013, filed in relation to EP1645631, 28 pages.
Decision of the board of appeal, filed in relation to appeal proceedings for EP1645631, dated Sep. 15, 2016, 37 pages.
Decision of the Board of Appeal, Filed in relation to appeal proceedings for EP2353608, Dated Nov. 20, 2018, 17 pages.
Decision of the Board of Appeal, filed in relation to appeal proceedings for EP2411048, dated Feb. 25, 2019, 13 pages.
Decision revoking EP1737486, filed in opposition against EP1737486, dated Oct. 28, 2015, 28 pages.
Decision revoking EP2258716, filed in opposition against EP2258716, dated Oct. 27, 2016, 15 pages.
Decision revoking EP2327719 during the opposition of EP2327719, dated Feb. 6, 2017, 18 pages.
Decision revoking the European Patent, filed in opposition against EP1976990, dated Nov. 11, 2013, 15 pages.

(56) References Cited

OTHER PUBLICATIONS

Decision to refuse a patent application, filed in the Opposition against EP1645631, dated Apr. 28, 2009, 7 pages.
Declaration (supplementary) by Prof. Paul Dunman, Ph.D., dated Sep. 25, 2012, submitted in opposition proceedings for EP1645631, 14 pages.
Declaration by Dr. Ellen Murphy, Ph.D., dated Sep. 14, 2011, submitted in opposition proceedings for EP1645631, 4 pages.
Declaration by Dr. Julian Parkhill dated Jun. 12, 2008, submitted in opposition proceedings for EP1645631, 2 pages.
Declaration by Dr. Julian Parkhill, filed in the Opposition against EP1645631, dated Jul. 10, 2014, 5 pages.
Declaration by E. Richard Moxon dated Feb. 16, 2013, submitted in opposition proceedings for EP1645631, 5 pages.
Declaration by Ellen Murphy, filed in the Opposition against EP1645631, dated May 12, 2014, 3 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by James Cleland Paton, dated Nov. 24, 2014, 16 pages.
Declaration by Prof. Paul Dunman, Ph.D., dated Sep. 13, 2011, submitted in opposition proceedings for EP1801219, 10 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Declaration of Dr. Leonard Mayer, filed in relation to EP1562983, dated Mar. 10, 2017, 3 pages.
Declaration of Dr. Loek van Alphen, filed in relation to EP1562983, dated Mar. 11, 2017, 9 pages.
Declaration of Dr. Wendell Zollinger, filed in relation to EP1562983, dated Mar. 13, 2017, 4 pages.
Declaration of Robert Donald, filed in opposition against EP1562983, dated Sep. 12, 2016, 3 pages.
Delgado et al. (2007). "Lipoprotein NMB0928 from Neisseria meningitidis serogroup B as a novel vaccine candidate," Vaccine 25:8420-8431.
Dintilhac and Claverys (1997). "The adc locus, which affects competence for genetic transformation in *Streptococcus pneumoniae*, encodes an ABC transporter with a putative lipoprotein homologous to a family of streptococcal adhesins," Res Microbiol 148:119-131.
Dlawer et al. (2010). "Human antibody responses to the meningococcal factor H binding protein LP2086 during invasive disease," 17th International Pathogenic Neisseria Conference 2010, p. 130.
Don et al. (1991). "'Touchdown' PCR to circumvent spurious priming during gene amplification," Nucleic Acids Res. 19(14):4008.
Donnelly et al. (2010). "Qualitative and quantitative assessment of meningococcal antigens to evaluate the potential strain coverage of protein-based vaccines," Proc Natl Acad Sci U S A, 107(45):19490-5.
Elzanowski et al. (2013). "The Genetic Codes, a compilation," Retrieved from http://www.bioinformatics.org/JaMBW/2/3/TranslationTables.html. 16 pages.
Excerpt of sequence data of 1997-12-15-NM.dbs, Enclosed to fourth declaration of Jullian Parkhill, Filed in opposition against EP1801219, Dated Aug. 22, 2016, 6 pages.
Experimental data: expression of NspA, fHBP and GNA2132 in N. meningitidis, filed in opposition against EP1534326, dated Aug. 4, 2010. 2 pages.
Experimental Report, Submitted on Mar. 23, 2015, filed in relation to EP2411048, 2 pages.
Expert Report of Professor John Heckels, UK High Court proceedings in *GlaxoSmithKline UK Limited* v. *Wyeth Holdings LLC*, dated Jan. 11, 2016, 82 pages.
Extracts from Expert Report of Professor John Heckels, UK High Court proceedings in *GlaxoSmithKline UK Limited* v. *Wyeth Holdings LLC*, dated Jan. 11, 2016, filed in opposition against EP2258716 and EP1562983, 8 pages.
Facts and Submissions dated May 21, 2012, in relation to EP1645631, 30 pages.
Farley et al. (2002). "Characterization, cloning and expression of different subfamilies of the ORF 2086 gene from Neisseria meningitidis," 13th International Pathogenic Neisseria Conference 2002, Poster, 15 pages.
Farley J. et al. (Sep. 2002). "Characterization, cloning and expression of different subfamilies of the ORF 2086 gene from Neisseria meningitidis," Thirteenth International Pathogenic Neisseria Conference, Norwegian Institute of Public Health, Oslo, Norway, p. 124.
Feavers et al. (2009). "Meningococcal protein antigens and vaccines," Vaccine 275:B42-B50.
Fleischmann et al. (1995). "Whole-Genome Random Sequencing and Assembly of Haemophilus influenzae Rd," Science 269:496-512.
Fletcher et al. (2004). "Vaccine Potential of the Neisseria meningitidis 2086 Lipoprotein," *Infection and Immunity* 72(4): 2088-2100.
Fontana et al. (2002). A genomic approach Abstract from the $13^{th}$ International Pathogenic Neisseria Conference, Oslo, Norway, Sep. 1-6, 2002. p. 248.
Fourth declaration of Julian Parkhill, filed in Relation to EP1645631, dated Aug. 25, 2016, 6 pages.
Fraser et al. (1997). "Genomic sequence of a lyme disease spirochaete, Borrelia burgdorferi," Nature 390:580-586.
Fraser et al. (1998). "Complete genome sequence of Treponema pallidum, the syphilis spirochete," Science 281:375-388.
Further submissions by patentee, dated Feb. 3, 2016, filed in relation to EP1645631 appeal, 9 pages.
Further Submissions in the opposition against EP1801219, filed on behalf of Pfizer Inc. dated Jul. 14, 2016. 3 pages.
Galeano et al. (1995). "Efectividad de una vacuna antimeningocócica en una cohorte de itagui, Colombia, 1995," Epidemiologico de Antioquia 20(2), 8 pages. (9 page English translation included).
Gene Browser, Nature Technology Corporation, filed in the Opposition against EP1645631, dated Jun. 26, 2013, 6 pages.
GenPept accession No. AAF42204, "hypothetical protein NMB1870 [Neisseria meningitidis MC58]," retrieved on Sep. 26, 2012, 2 pages.
Gil et al. (2009). "Proteomic study via a non-gel based approach of meningococcal outer membrane vesicle vaccine obtained from strain CU385," Human Vaccines 5(5):347-356.
Giuliani et al. (2006). "A universal vaccine for serogroup B meningococcus," PNAS 103(29):10834-10839.
Giuliani et al. (2010). "Measuring antigen-specific bactericidal responses to a multicomponent vaccine against serogroup B meningococcus," Vaccine 28:5023-5030.
Giuliani et al. (Feb. 2005). "The Region Comprising Amino Acids 100 to 255 of Neisseria meningitidis Lipoprotein GNA 1870 Elicits Bactericidal Antibodies," *Infection and Immunity* 73(2): 1151-1160.
Gold and Stormo (1987). "Translation Initiation", in *Escherichia* con and *Salmonella typhimurium*, Cellular and Molecular Biology, Ed. Neidhardt, pp. 1302-1307.
Gorringe & Pajon (2012) "Bexsero: a multicomponent vaccine for prevention of meningococcal disease." Human Vaccines & Immunotherapeutics 8:1-10.
Gorringe et al. (2009). "16th International Pathogenic Neisseria Conference: recent progress towards effective meningococcal disease vaccines," Human Vaccines 5(2):53-56.
Grandi (2005). "Reverse vaccinology: a critical analysis," in Encyclopedia of Genetics, Genomics, Proteomics and Bioinformatics, pp. 1322-1326.
Granoff, DM. (2009). Relative importance of complement-mediated bactericidal and opsonic activity for protection against meningococcal disease. Vaccine 27(Supplement 2): B117-B125.
Great Britain Application No. 0121591.2, Filed Sep. 6, 2001, Entitled "Hybrid and tandem expression of neisserial proteins," Applicant Chiron S.p.A., 54 pages.
Great Britain patent application No. 0227346.4, filed Nov. 22, 2003, entitled "741," by applicant Chiron SpA.
Harris et al. (2008). "Development and qualification of serum bactericidal assays for Neisseria meningitidis serogroup B," 16th International Pathogenic Neisseria Conference 2008, p. 268-269.

(56) References Cited

OTHER PUBLICATIONS

Harris et al. (2010). "Robustness of the Serum Bactericidal Activity (SBA) Assay for Neisseria meningitidis serogroup B," 17th International Pathogenic Neisseria Conference 2010, p. 169.
Harris et al. (2011) "Preclinical evidence for the potential of a bivalent fHBP vaccine to prevent Neisseria meningitidis serogroup C disease," Human Vaccines 7 Suppl:68-74.
Hayashi and Wu, "Identification and characterization of lipid-modified proteins in bacteria," Chapter 10 in Lipid Modifications of Proteins: A Practical Approach, Hooper and Turner (eds.), published in 1992, 27 pages.
Hem et al. (1995). "Structure and properties of aluminum-containing adjuvants," Vaccine Design. Subunit and Adjuvant Approach, pp. 249-276.
Hodge et al. (2006). "Development of a luminex-based meningococcal rLP2086-specific human IgG assay," 15th International Pathogenic Neisseria Conference 2006, p. 113.
Hoiseth et al. (2008). "LP2086 and MLST distribution in epidemiologically relevant strains of serogroup B Neisseria meningitidis," 16th International Pathogenic Neisseria Conference 2008, p. 205.
Holst et al. (2014). "Variability of genes encoding surface proteins used as vaccine antigens in meningococcal endemic and epidemic strain panels from Norway," Vaccine 32:2722-2731.
Hou et al. (2005) "Protective antibody responses elicited by a meningococcal outer membrane vesicle vaccine with overexpressed genome-derived neisserial antigen 1870," J Infect Dis 192(4):580-90.
Hung et al. (2011). "The Neisseria meningitidis macrophage infectivity potentiator protein induces cross-strain serum bactericidal activity and is a potential serogroup B vaccine candidate," Infect Immun 79(9):3784-3791.
Interlocutory decision in opposition proceedings, filed in the Opposition against EP1645631, dated May 21, 2012, 82 pages.
Interlocutory decision, filed in opposition against EP1562983, dated Nov. 4, 2016, 16 pages.
Jacobsson et al. (2009). "Prevalence and sequence variations of the genes encoding the five antigens included in the novel 5CVMB vaccine covering group B meningococcal disease" Vaccine. 27:1579-1584.
Jansen et al. (2008). "Bivalent recombinant LP2086 vaccine to provide broad protection against Neisseria meningitidis B disease: immunological correlates of protection and how to assess coverage against invasive MnB strains," 16th International Pathogenic Neisseria Conference 2008, p. 80-81.
Jansen et al. (2009). "Development of a bivalent factor H binding protein vaccine to broadly protect against invasive Neisseria meningitides serogroup B (MnB) disease," European Society for Paediatric Infectious Disease Symposium 2009, p. 311.
Jansen et al. (2010). "Estimating effectiveness for Neisseria meningitidis serogroup B (MnB) vaccine candidates composed of non-serogroup specific antigens," 17th International Pathogenic Neisseria Conference 2010, p. 37.
Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.
JCVI-CMR website showing Z2491 Sanger sequence (http://cmr.jcvi.org/tigr-scripts/CMR/shared/Genomes.cgi and links). (2010) 8 pages.
Jiang et al. (2003). "Using rate of acid neutralization to characterize aluminum phosphate adjuvant," Pharma Dev Tech 8(4):349-356.
Jiang et al. (2006). "Serum IgG response induced by a bivalent recombinant LP2086 provides broad protection against serogroup B Neisseria meningitidis," 15th International Pathogenic Neisseria Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic Neisseria Conference 2008, p. 57-58.

Jiang et al., (2010) "Broad vaccine coverage predicted for a bivalent recombinant factor H binding protein based vaccine to prevent serogroup B meningococcal disease" Vaccine 28:6086-6093.
Johnson et al. (1999). "Analysis of the human Ig isotype response to lactoferrin binding protein A from Neisseria meningitidis," FEMS Immun. Med. Microbial. 25(4): 349-354.
Jones et al. (2005). "Effects of adsorption to aluminum salt adjuvants on the structure and stability of model protein antigens," J Biol Chem 280(14):13406-13414.
Jones et al. (2009). "Generation of human serum complement lots that perform consistently for use in Neisseria meningitidis serogroup B (MnB) vaccine clinical trials," European Society for Paediatric Infectious Disease Symposium 2009, p. 566.
Jongerius et al. (2013) "Distinct binding and immunogenic properties of the gonococcal homologue of meningococcal factor h binding protein," PLOS Pathogens. 9(8):e1003528 pp. 1.
Juncker et al. (2003). "Prediction of lipoprotein signal peptides in gram-negative bacteria," Protein Sci 12:1652-1662.
Kimura et al. (2011) "Immunogenicity and Safety of a Multicomponent Meningococcal Serogroup B Vaccine and a Quadrivalent Meningococcal CRM197 Conjugate Vaccine against Serogroups A, C, W-135, and Y in Adults Who Are at Increased Risk for Occupational Exposure to Meningococcal Isolates" Clin. Vaccine Immunol. 18(3):483-486.
Klein et al. (2000). "Analysis of aluminum hydroxyphosphate vaccine adjuvants by 27Al MAS NMR," J Pharma Sci 89(3):311-321.
Koeberling et al. (2007). "Improved immunogenicity of a H44/76 group B outer membrane vesicle vaccine with over-expressed genome-derived Neisserial antigen 1870," Vaccine 25(10):1912-1920.
Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Kovacs-Simon et al. (2011). "Lipoproteins of Bacterial Pathogens," Infect Immun 79(2):548-561.
Lee et al. (1990). "cDNA Cloning Using Degenerate primers," in "PCR Protocols: A Guide to Methods and Applications," Innis et al. (Eds.), pp. 46-53, Academic Press, San diego.
Lewis et al. (2010). "The meningococcal vaccine candidate neisserial surface protein A (NspA) binds to factor H and enhances meningococcal resistance to complement," PLoS Pathogens 6(7):e1001027. 20 pages.
Liebl et al. (1997). "Properties and gene structure of the Thermotoga maritima alpha-amylase AmyA, a putative lipoprotein of a hyperthermophilic bacterium," J Bacteriol 179(3):941-948.
Liechti et al. (2012). "Outer membrane biogenesis in *Escherichia coli*, Neisseria meningitidis, and Helicobacter pylori: paradigm deviations in H. pylori," Front Cell and Infect Microbiol 2:article 29. 18 pages.
Lindblad, (2004). "Aluminium compounds for use in vaccines," Immunol Cell Biol.,82(5):497-505.
Lucidarme et al., (2010). "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Madico et al. (2006). "The meningococcal vaccine candidate GNA1870 binds the complement regulatory protein factor H and enhances serum resistance," J Immunol 177(1):501-510.
Marshall et al. (2008). "A randomized, placebo-controlled, double-blind, phase 1 trial of ascending doses of meningococcal group B

(56) References Cited

OTHER PUBLICATIONS rLP2086 vaccine in healthy adults," 16th International Pathogenic Neisseria Conference 2008, p. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.
Marshall et al. (2013) "A phase 2 open-label safety and immunogenicity study of a meningococcal B bivalent rLP2086 vaccine in healthy adults," Vaccine 31:1569-75.
Mascioni et al. (2008). "Determination of the domain and solution structure of rLP2086, a meningococcal vaccine candidate and human factor H binding protein," 16th International Pathogenic Neisseria Conference 2008, p. 77-78.
Mascioni et al. (2009) "Structural basis for the immunogenic properties of the meningococcal vaccine candidate LP2086," J Biol Chem 284:8738-46.
Mascioni et al. (2010) "NMR dynamics and antibody recognition of the meningococcal lipidated outer membrane protein LP2086 in micellar solution," Biochim Biophys Acta 1798:87-93.
Masignani V. (Mar. 17, 2003). "Vaccination against Neisseria meningitidis using three variants of the lipoprotein GNA1870," J. Exp. Med. 197(6):789-799.
McNeil et al. (2009) "Detection of LP2086 on the cell surface of Neisseria meningitidis and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic Neisseria Conference 2010, p. 94.
McNeil et al. (2013) "Role of factor H binding protein in Neisseria meningitidis virulence and its potential as a vaccine candidate to broadly protect against meningococcal disease," Microbiol Mol Biol Rev 77:234.
Meyer et al. (1984). "Pilus genes of Neisseria gonorrheae: Chromosomal organization and DNA sequence," Proc. Natl. Acad. Sci. USA 81: 6110-6114.
Milagres et al. (1998). "Specificity of bactericidal antibody response to serogroup B meningococcal strains in Brazilian children after immunization with an outer membrane vaccine," Infection and Immun. 66(10): 4755-4781.
Minutes of the oral proceedings before the board of appeal, filed in opposition against EP1645631, dated Sep. 15, 2016, 5 pages.
Minutes of the oral proceedings, filed in the Opposition against EP1645631, dated Feb. 11, 2014, 4 pages.
Morley, S. et al. (Dec. 12, 2001). "Vaccine prevention of meningococcal disease, coming soon?" *Vaccine* 20(5-6):666-687.
Munkley, et al. (1991). "Blocking of bactericidal killing of Neisseria meningitidis by antibodies directed against slacc 4 outer membrane proteins," Microbial Pathogenesis 11: 447-452.
Murphy et al. (2008). "Sequence diversity of vaccine candidate LP2086 in Neisseria meningitidis serogroup B strains causing invasive disease," 16th International Pathogenic Neisseria Conference 2008, p. 61.
Murphy et al. (2010). "Prevalence of Factor H Binding Protein (fHBP) Variants in N. meningitidis Carriage Isolates," 17th International Pathogenic Neisseria Conference 2010, p. 96.
Murphy et al., (2009) "Sequence diversity of the factor H binding protein vaccine candidate in epidemiologically relevant strains of serogroup B Neisseria meningitidis" J Infect Dis 200:379-389.
Nassif (2000). "A Furtive Pathogen Revealed," Science 287:1767-1768.
NMA0586 (D79b), filed in relation to EP1645631 on Sep. 2, 2016, 9 pages.
Notice of Appeal by GlaxoSmithKline Biologicals S.A., filed in relation to EP2327719, dated Mar. 24, 2017, 6 pages.
Notice of Opposition against EP 1562983, filed on Jul. 1, 2014, 23 pages.
Notice of Opposition against EP1645631, filed in the Opposition against EP1645631, dated Jul. 23, 2008, 25 pages.
Notice of Opposition against EP1801219, filed on behalf of Pfizer Inc. dated Jul. 14, 2016. 54 pages.
Notice of opposition against EP2343308, filed in opposition against EP1562983, submitted Jan. 11, 2016, 21 pages.
Notice of Opposition filed May 24, 2012, filed in opposition against EP1976990, 19 pages.
Notice of opposition, filed in opposition against EP2258716, dated Apr. 16, 2015, 12 pages.
Notice of opposition, filed in opposition against EP2327719, dated May 20, 2015, 14 pages.
Novartis (Jan. 22, 2013) "Novartis receives EU approval for Bexsero®, first vaccine to prevent the leading cause of life-threatening meningitis across Europe," Media Release, 3 pages.
Novartis (Jun. 9, 2011). "Novartis candidate vaccine Bexsero® shows significant potential in providing broad coverage against meningococcal serogroup B infections." Media Release, 6 pages.
Novartis (Oct. 9, 2008) "New Phase II data show Novartis investigational Meningitis B vaccine may also protect infants six months and older," Media Release, 4 pages.
Novartis internal data, filed in relation to EP1902726, submitted on Apr. 13, 2015, 1 page.
Ochman et al. (1990). "Amplification of flanking sequences by inverse PCR," in "PCR Protocols: A Guide to Methods and Applications," Innis et al. (Eds.), pp. 219-227, Academic Press, San diego.
Ochoa, Rolando (2008). "Main projects on research, development and manufacturing of human vaccines," excerpt from presentation at BioQatar Symposium 2008, 4 slides.
Opponent's Further Submission in Preparation of the Oral Proceedings, filed in the Opposition against EP1645631, dated Nov. 3, 2011, 6 pages.
Opponent's Response to the Patentee's Grounds of Appeal, filed in the Opposition against EP1737486 on Jul. 20, 2016, 19 pages.
Opponent's Response to the Patentee's Submission dated Feb. 18, 2013, filed in the Opposition against EP1645631, dated Jul. 24 2014, 34 pages.
Opponents Final Written Submission in Preparation of Oral Proceedings, filed in the Opposition against EP1645631, dated Sep. 14, 2011, 28 pages.
ORF Finder (2013). "Bacterial Code," Retrieved from http://www.ncbi.nlm.nih.gov/gorf/gorf.html, 3 pages.
ORF Finder result for NMB1870 sequence with upstream sequence, chromosome ASM880v1, accessed Sep. 27, 2012, submitted in the opposition proceedings for EP1801219. 2 pages.
Pajon et al. (2010). "Frequency of factor H-binding protein modular groups and susceptibility to cross-reactive bactericidal activity in invasive meningococcal isolates" Vaccine 28:2122-2129.
Pajon et al. (2011). "Meningococcal factor H binding proteins in epidemic strains from Africa: implications for vaccine development," PLoS Negl Trop Dis. 5(9):e1302.
Pajon et al. (2012). "Design of meningococcal factor H binding protein mutant vaccines that do not bind human complement factor H," Infect Immun 80:2667-2677.
Parkhill et al. (2000). "Complete DNA Sequence of a Serogroup A Strain of Neisseria meningitides Z2491," Nature, 404(6777):502-506.
Parkhill, "Campylobacter jejuni genome sequence at the Sanger Centre," Post on BIOSCI/Bionet of May 8, 1998. 1 page.
Patentee's response to notice of opposition, filed in opposition against EP1562983, dated Feb. 16, 2015, 9 pages.
Patentee's Submissions under Rule 116 EPC, filed in the Opposition against EP1645631, dated Sep. 13, 2011, 13 pages.
Patentee's submission of amended description, filed in relation to post-appeal proceedings for EP1645631, dated Feb. 17, 2017. 19 pages.
Patentee's submissions, filed in relation to appeal proceedings for EP1737486, dated Dec. 1, 2016, 5 pages.

(56) References Cited

OTHER PUBLICATIONS

Patentees' Response to Opposition, filed in opposition against European Patent EP1645631, dated May 8, 2009, 13 pages.
Perez et al. (2010). "Community acquired bacterial meningitis in Cuba: a follow up of a decade," BMC Infectious Diseases 10:130, 9 pages.
Pettersson, et al. (2006). "Vaccine potential of the Neisseria meningitidis lactoferrin-binding proteins LbpA and LbpB," Vaccine 24(17):3545-3557.
Pfizer observations, filed in opposition against EP1562983, dated Apr. 27, 2012, 7 pages.
Pfizer observations, filed in opposition against EP1562983, dated May 12, 2011, 7 pages.
Pfizer's submissions in opposition against EP2343308, dated May 2, 2016, filed in opposition against EP1562983, 33 pages.
Pillai et al. (2005) "Outer membrane protein (OMP) based vaccine for Neisseria meningitidis serogroup B," Vaccine 23(17-18):2206-2209.
Pizza et al. (2000). "Identification of Vaccine Candidates Against Serogroup B Meningococcus by Whole-Genome Sequencing," Science 287(5459):1816-1820.
Pizza et al. (2008) "Factor H-binding protein, a unique meningococcal vaccine antigen" Vaccine 26S:I46-8.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Priority document for U.S. Appl. No. 60/162,616, filed Oct. 29, 1999. 1 page.
Progress through the Sanger Institute FTP server (May 12, 2009), 15 pages.
Prosite, "ScanProsite Results Viewer: USERSEQ1 (280aa)," retrieved on Jun. 21, 2012, 1 page.
PSORT analysis of 200 of the sequences disclosed in PCT/US99/09346 (Jan. 1, 2010), 209 pages.
PSORT analysis of Seq ID Nos. 4 and 6, and of 'Contig295' 300mer (May 8, 2009), 5 pages.
PSORT analysis of the sequence related to orf741 from the 'second' ATG, "D5 / D20 / D20A ORF", accessed Jun. 22, 2012, submitted in the opposition proceedings for EP1801219. 1 page.
PSORT analysis of the sequence related to orf741 from the 'second' ATG, "MENB 'Second' ATG Start" accessed Sep. 27, 2012, submitted in the opposition proceedings for EP1801219. 1 page.
PSORT prediction result for Seq ID No. 2 (Mar. 30, 2010), 1 page.
Pugsley (1993). "The complete general secretory pathway in gram-negative bacteria," Microbiological Rev 5(1):50-108.
Response by opponent, filed in opposition against EP1562983, dated Jan. 11, 2016, 12 pages.
Response by patentee, dated Jul. 28, 2016, filed in opposition against EP1562983, 4 pages.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Response to Communication, filed in EP Application No. 07075161.5. Oct. 28, 2009. 2 pages.
Response to Notice of Opposition by Novartis Vaccines and Diagnostics SRL for EP2327719, dated Jan. 6, 2016. 10 pages.
Response to notice of opposition, Filed in opposition against EP1801219, Dated Dec. 30, 2016, 6 pages.
Response to Notice of Opposition, filed in opposition against EP2258716, dated Dec. 3, 2015, 8 pages.
Result from "Hphob. / Hopp & Woods" using the Seq ID No. 4 and Seq ID No. 6 from WO 99/57280, accessed Jul. 13, 2016, submitted in the opposition proceedings of EP1801219. 2 pages.
Richmond et al. (2008). "A randomized, observer-blinded, active control, phase 1 trial of meningococcal serogroup B rLP2086 vaccine in healthy children and adolescents aged 8 to 14 years," 16th International Pathogenic Neisseria Conference 2008, p. 270-271.
Richmond et al. (2010). "Safety & immunogenicity of serogroup B Neisseria meningitidis (MnB) rLP2086 vaccine in adults and adolescent subjects: overview of 3 clinical trials," 17th International Pathogenic Neisseria Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent Neisseria meningitidis recombinant lipidated factor H binding protein vaccine in young adults: Results of a randomized, controlled, dose-escalation phase 1 trial," Vaccine 30(43):6163-74.
Richmond et al. (2012) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Rinaudo et al. (2009). "Vaccinology in the genome era", The Journal of Clinical Investigation, 119(9):2515-2525.
Rodriguez et al. (1999). "The epidemiological impact of antimeningococcal B vaccination in Cuba," Mem Inst Oswaldo Cruz 94(4):433-440.
Sandbu et al. (2007). "Immunogenicity and safety of a combination of two serogroup B meningococcal outer membrane vesicle vaccines," Clin Vaccine Immunol, 14(9):1062-9.
Sanger Centre's "Projects" website as of Dec. 10, 1997 as retrievable via http://web.archive.org. 1 page.
Santolaya et al. (2012) "Immunogenicity and tolerability of a multicomponent meningococcal serogroup B (4CMenB) vaccine in healthy adolescents in Chile: a phase 2b/3 randomised, observer-blind, placebo-controlled study," Lancet. 379(9816):617-24.
Scarselli et al. (Feb. 13, 2009). "Epitope Mapping of a Bactericidal Monoclonal Antibody against the Factor H Binding Protein of Neisseria meningitides," Journal of Molecular Biology 386(1):97-108.
Schild et al. (1996). "Peptide Based Vaccines," in "Concepts in Vaccine Development," Kaufmann (Ed.), pp. 303-326, De Gruyter.
Schneider et al. (Apr. 16, 2009) "Neisseria meningitidis recruits factor H using protein mimicry of host carbohydrates," Nature 458(7240):890-893.
Seeber et al. (1991). "Predicting the adsorption of proteins by aluminum-containing adjuvants," Vaccine 9(3):201-203.
Seib et al. (2010). "Influence of serogroup B meningococcal vaccine antigens on growth and survival of the meningococcus in vitro and in ex vivo and in vivo models of infection," Vaccine 28(12):2416-2427.
Seib et al. (2011). "Characterization of Diverse Subvariants of the Meningococcal Factor H (fH) Binding Protein for Their Ability to Bind fH, to Mediate Serum Resistance, and to Induce Bactericidal Antibodies," Infect Immun, 79(2):970-81.
Sequence for "Putative Lipoprotein [*Neisseria meningitidis* Z2491]," NCBI Reference Sequence: YP_002342062.1, Mar. 30, 2000. 2 pages.
Sequence NMA0586 from "741 ORF found using Sanger sequence with ORFFinder", with upstream sequence from Bacterial Emsembl, Submitted in the opposition proceedings of EP1801219 on Jul. 14, 2016. 2 pages.
Serruto et al. (2009). "Genome-based approaches to develop vaccines against bacterial pathogens," Vaccine 27:3245-3250.
Serruto et al. (2012). "The new multicomponent vaccine against meningococcal serogroup B, 4CMenB: immunological, functional and structural characterization of the antigens," Vaccine. 30(0 2):B87-B97.
Sheldon et al. (2011). "Phase 1, Randomized, Open-Label, Study to Assess the Safety and Immunogenicity of Serogroup B Neisseria Meningitidis (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of Erwinia chrysanthemi 3937," Mole Microbiol 19(3):455-466.

(56) References Cited

OTHER PUBLICATIONS

Sierra GV, et al. (1991). Vaccine against group B Neisseria meningitidis: protection trial and mass vaccination results in Cuba. NIPH Ann 14: 195-207.
Sprengart et al. (1997). "Functional importance of RNA interactions in selection of translation initiation codons," Molecular Microbiology, 24(1): 19-28.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Statement of Grounds of Appeal, dated Mar. 23, 2015, filed in relation to EP2411048, 8 pages.
Statement of grounds of appeal, dated Mar. 7, 2016, filed in relation to EP1737486, 9 pages.
Statement of grounds of appeal, filed in relation to EP1562983, Dated Mar. 14, 2017, 20 pages.
Statement of grounds of appeal, filed in relation to EP1902726, dated Apr. 13, 2015, 9 pages.
Statement of Grounds of Appeal, filed in relation to EP2353608, dated Jul. 22, 2015, 8 pages.
Submission by Novartis, filed in opposition against EP2327719, dated Oct. 25, 2016, 9 pages.
Submission by Pfizer in preparation to oral proceedings, filed in opposition against EP2327719, dated Nov. 16, 2016, 7 pages.
Submission by Pfizer, filed in opposition against EP2327719, dated Oct. 25, 2016, 28 pages.
Submission in opposition proceedings by Carpmaels and Ransford filed in EP1737486 on Jun. 12, 2015, 2 pages.
Submission in opposition proceedings by Pfizer Inc. filed against EP1737486 on Jun. 12, 2015, 7 pages.
Submission of the Patentee of Jul. 6, 2012, filed Jun. 24, 2014, in the Opposition against EP1645631, 4 pages.
Submissions by opponent, Wyeth LLC, filed in relation to EP1645631, dated Sep. 1, 2016, 19 pages.
Submissions by patentee, GlaxoSmithKline Biologicals SA, filed in relation to EP1645631 on Aug. 15, 2016, 16 pages.
Summons to Attend Oral Hearings dated Jan. 29, 2014, for EP App. No. 10713516, 13 pages.
Summons to oral proceedings pursuant to Rule 115(1) EPC, filed in the Opposition against EP1645631, dated Nov. 11, 2013, 12 pages.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Supplementary declaration by Ellen Murphy dated Sep. 26, 2012, submitted in opposition proceedings for EP1645631, 3 pages.
Supplementary material Table and Figure for "NM0586" of Parkhill et al., 2000, Nature. 28 pages.
Supplementary Submission to the Grounds of Appeal, filed in the Opposition against EP1645631, dated Sep. 28, 2012, 2 pages.
Sutcliffe and Russell (1995). "Lipoproteins of gram-positive bacteria," J Bacteriol 177(5):1123-1128.
Swaminathan (1996). "Molecular cloning of the three base restriction endonuclease R.CviJl from eukaryotic Chlorella virus IL-3A," Nucleic Acids Research, 24(13): 2463-2469.
Sworn Statement in EP1645631 from Isabel Delany, signed Feb. 1, 2016. 2 pages.
Tan et al. (2010). "Advances in the development of vaccines against Neisseria meningitidis," NEJM 362(16):1511-1520.
Telford et al. (2003). "Genomic and Proteomics in Vaccine Design", in *New Bacterial Vaccines*, edited by Ellis et al. Kleweur Academic/Plenum Publishers, USA. pp. 1-11.
Tettelin et al. (Mar. 10, 2000). "Complete Genome Sequence of Neisseria meningitidis Serogroup B Strain MC58," Science 287(5459):1809-1815.
The printed output from the NCBI open reading frame finder (Oct. 20, 2008), 12 pages.

TIGR Microbial Database, filed in the Opposition against EP1645631, dated Jun. 20, 2012, 14 pages.
TIGR website as of 1998, 8 pages.
UK High Court Claim Form, Claimant Pfizer, Inc., Defendant GlaxoSmithKline Biologicals S.A., submitted Mar. 24, 2017 in opposition against EP1801219, 4 pages.
UniProt accession No. C0JF81, Murphy et al., Last modified on May 5, 2009. 4 pages.
United States Office Action dated Feb. 11, 2009, for U.S. Appl. No. 10/181,600, filed Jan. 17, 2001, 5 pages.
United States Office Action dated Jul. 24, 2008, for U.S. Appl. No. 10/181,600, filed Jan. 17, 2001, 23 pages.
United States Office Action dated Jul. 7, 2009, for U.S. Appl. No. 10/181,600, filed Jan. 17, 2001, 23 pages.
U.S. Appl. No. 60/098,685, "*Neisseria* Spp, Polypeptide, Gene Sequence and Uses Thereof," filed Sep. 1, 1998. 82 pages.
U.S. Appl. No. 60/328,101, "Novel immunogenic compositions for the prevention and treatment of meningococcal disease," filed Oct. 11, 2001. 253 pages.
U.S. Appl. No. 60/406,934, "Novel immunogenic compositions for the prevention and treatment of meningococcal disease," filed Aug. 30, 2002. 190 pages.
U.S. Appl. No. 60/647,911, "GNA 1870-based vesicle vaccines for broad spectrum protection against diseases caused by Neisseria meningitidis," filed Jan. 27, 2005. 99 pages.
U.S. Appl. No. 61/358,816, "Combinations of Meningococcal Factor H Binding Proteins," filed Jun. 25, 2010. 48 pages.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.
Von Heijne (1989). "The structure of signal peptides from bacterial lipoproteins," Protein Engineering 2(7):531-534.
Voulhoux and Tommassen (2002). "Transport of lipoproteins to the cell surface in Neisseria meningitidis," 13th International Pathogenic Neisseria Conference 2002, p. 31.
Vu et al. (2011). "Cooperative serum bactericidal activity between human antibodies to meningococcal factor H binding protein and neisserial heparin binding antigen," Vaccine. 24;29(10):1968-73.
Vu et al. (2012) "A Broadly Cross-Reactive Monoclonal Antibody Against an Epitope on the N-terminus of Meningococcal fHbp" Sci Rep. 2: 341, pp. 1-8.
Wang et al. (2010). "Prevalence and genetic diversity of candidate vaccine antigens among invasive Neisseria meningitidis isolates in the United States," 17th International Pathogenic Neisseria Conference 2010, p. 122.
Welsch et al. (2004). "Protective Activity of Monoclonal Antibodies to Genome-Derived Neisserial Antigen 1870, a Neisseria meningitidis Candidate Vaccine," *The Journal of Immunology* 172: 5606-5615.
Welsch et al. (2007) "A novel mechanism for complement-mediated killing of encapsulated Neisseria meningitidis elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Withdrawal of Appeal by patentee, filed in relation to EP2327719, dated May 31, 2017, 1 page.
Withdrawal of Opposition by Pfizer Inc., filed in opposition against EP2327719, dated May 2, 2017, 1 page.
Withdrawal of opposition, filed in relation to EP1562983, dated May 2, 2017, 1 page.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Written Submission to Oral Proceedings, filed in opposition against EP1976990, dated Jul. 24, 2013, 11 pages.
Written Submissions from the Patentee, GlaxoSmithKline Biologicals SA for EP1645631, dated Feb. 3, 2016, 10 pages.

(56) References Cited

OTHER PUBLICATIONS

Wu et al. (1996). "A protein class database organized with ProSite protein groups and PIR superfamilies," J Comp Biol 3(4):547-561.

York et al. (2010). "fHBP epidemiology of invasive meningococcal B isolates from Spain and Germany: age based," 17th International Pathogenic Neisseria Conference 2010, p. 109.

Zhou et al. (2000). "Universal TA cloning," Curr Issues Mol Biol. 2(1):1-7.

Zhu et al. (2004). "Evaluation of the purified recombinant lipidated P2086 protein as a vaccine candidate for group B Neisseria meningitidis in a murine nasal challenge model," 14th International Pathogenic Neisseria Conference 2004, p. 199.

Zhu et al. (2005) "Evaluation of recombinant lipidated P2086 protein as a vaccine candidate for group B Neisseria meningitidis in a murine nasal challenge model," Infect Immun 73(10):6838-45.

Zhu et al. (2006) "Intranasal immunization of mice with recombinant lipidated P2086 protein reduces nasal colonization of group B Neisseria meningitidis," Vaccine 24:5420-5.

Zhu et al. (2006). "Effective immunization strategy against group B Neisseria meningitidis using purified recombinant lipidated P2086 protein," 15th International Pathogenic Neisseria Conference 2006, p. 47.

Zlotnick et al. (2009). "Epidemiology of the serogroup B Neisseria meningitidis (MnB) factor H binding protein in strains sampled from Spain and Germany in the years 2001-2006," 10th European Meningococcal Disease Society Congress 2009, p. 81.

Zlotnick et al. (2010). "Biochemical and biophysical analysis indicates conformation plays an important role in the binding of hfH and antibodies to the fHBP of N. meningitidis," 17th International Pathogenic Neisseria Conference 2010, p. 38.

Zollinger et al. (2010). "Design and evaluation in mice of a broadly protective meningococcal group B native outer membrane vesicle vaccine," Vaccine, 28(31):5057-5067.

SEQUENCE LISTING

<160> NUMBER OF SEQ ID NOS: 25

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr

```
                145                 150                 155                 160
Tyr Thr Ile Asp Phe Ala Ala Lys Gln Gly Asn Gly Lys Ile Glu His
                165                 170                 175
Leu Lys Ser Pro Glu Leu Asn Val Asp Leu Ala Ala Ala Asp Ile Lys
                180                 185                 190
Pro Asp Gly Lys Arg His Ala Val Ile Ser Gly Ser Val Leu Tyr Asn
                195                 200                 205
Gln Ala Glu Lys Gly Ser Tyr Ser Leu Gly Ile Phe Gly Gly Lys Ala
                210                 215                 220
Gln Glu Val Ala Gly Ser Ala Glu Val Lys Thr Val Asn Gly Ile Arg
225                 230                 235                 240
His Ile Gly Leu Ala Ala Lys Gln
                245

<210> SEQ ID NO 2
<211> LENGTH: 247
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
1               5                   10                  15
Leu Asp His Lys Asp Lys Ser Leu Gln Ser Leu Thr Leu Asp Gln Ser
                20                  25                  30
Val Arg Lys Asn Glu Lys Leu Lys Leu Ala Ala Gln Gly Ala Glu Lys
                35                  40                  45
Thr Tyr Gly Asn Gly Asp Ser Leu Asn Thr Gly Lys Leu Lys Asn Asp
                50                  55                  60
Lys Val Ser Arg Phe Asp Phe Ile Arg Gln Ile Glu Val Asp Gly Gln
65                  70                  75                  80
Leu Ile Thr Leu Glu Ser Gly Glu Phe Gln Ile Tyr Lys Gln Asp His
                85                  90                  95
Ser Ala Val Val Ala Leu Gln Ile Glu Lys Ile Asn Asn Pro Asp Lys
                100                 105                 110
Ile Asp Ser Leu Ile Asn Gln Arg Ser Phe Leu Val Ser Gly Leu Gly
                115                 120                 125
Gly Glu His Thr Ala Phe Asn Gln Leu Pro Asp Gly Lys Ala Glu Tyr
                130                 135                 140
His Gly Lys Ala Phe Ser Ser Asp Asp Ala Gly Gly Lys Leu Thr Tyr
145                 150                 155                 160
Thr Ile Asp Phe Ala Ala Lys Gln Gly His Gly Lys Ile Glu His Leu
                165                 170                 175
Lys Thr Pro Glu Gln Asn Val Glu Leu Ala Ala Ala Glu Leu Lys Ala
                180                 185                 190
Asp Glu Lys Ser His Ala Val Ile Leu Gly Asp Thr Arg Tyr Gly Ser
                195                 200                 205
Glu Glu Lys Gly Thr Tyr His Leu Ala Leu Phe Gly Asp Arg Ala Gln
                210                 215                 220
Glu Ile Ala Gly Ser Ala Thr Val Lys Ile Gly Glu Lys Val His Glu
225                 230                 235                 240
Ile Gly Ile Ala Gly Lys Gln
                245

<210> SEQ ID NO 3
<211> LENGTH: 250
```

```
<212> TYPE: PRT
<213> ORGANISM: Neisseria meningitidis

<400> SEQUENCE: 3

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 4
<211> LENGTH: 248
<212> TYPE: PRT
<213> ORGANISM: Neisseria meningitidis

<400> SEQUENCE: 4

Val Thr Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95
```

```
Ser Ala Leu Thr Ala Leu Gln Thr Glu Gln Gln Asp Pro Glu His
            100                 105                 110

Ser Glu Lys Met Val Ala Lys Arg Arg Phe Arg Ile Gly Asp Ile Ala
115                 120                 125

Gly Glu His Thr Ser Phe Asp Lys Leu Pro Lys Asp Val Met Ala Thr
            130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Asp Leu Ala Val Ala Tyr Ile Lys
            180                 185                 190

Pro Asp Glu Lys His His Ala Val Ile Ser Gly Ser Val Leu Tyr Asn
        195                 200                 205

Gln Asp Glu Lys Gly Ser Tyr Ser Leu Gly Ile Phe Gly Glu Lys Ala
    210                 215                 220

Gln Glu Val Ala Gly Ser Ala Glu Val Glu Thr Ala Asn Gly Ile His
225                 230                 235                 240

His Ile Gly Leu Ala Ala Lys Gln
                245

<210> SEQ ID NO 5
<211> LENGTH: 250
<212> TYPE: PRT
<213> ORGANISM: Neisseria meningitidis

<400> SEQUENCE: 5

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Asp Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Ala Ala Lys Gln Gly His Gly Lys Ile
                165                 170                 175

Glu His Leu Lys Ser Pro Glu Leu Asn Val Asp Leu Ala Ala Ala Asp
            180                 185                 190

Ile Lys Pro Asp Glu Lys His His Ala Val Ile Ser Gly Ser Val Leu
        195                 200                 205

Tyr Asn Gln Ala Glu Lys Gly Ser Tyr Ser Leu Gly Ile Phe Gly Gly
    210                 215                 220
```

```
Gln Ala Gln Glu Val Ala Gly Ser Ala Glu Val Thr Ala Asn Gly
225                 230                 235                 240

Ile Arg His Ile Gly Leu Ala Ala Lys Gln
                245                 250
```

<210> SEQ ID NO 6
<211> LENGTH: 250
<212> TYPE: PRT
<213> ORGANISM: Neisseria meningitidis

<400> SEQUENCE: 6

```
Val Ala Ala Asp Ile Gly Thr Gly Leu Ala Asp Leu Thr Ala Pro
1               5                   10                  15

Leu Asp His Lys Asp Lys Gly Leu Lys Ser Leu Thr Leu Glu Asp Ser
                20                  25                  30

Ile Ser Gln Asn Gly Thr Leu Thr Leu Ser Ala Gln Gly Ala Glu Lys
                35                  40                  45

Thr Phe Lys Val Gly Asp Lys Asp Asn Ser Leu Asn Thr Gly Lys Leu
        50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asp His Ser Ala Val Val Ala Leu Gln Ile Glu Lys Ile Asn Asn
                100                 105                 110

Pro Asp Lys Ile Asp Ser Leu Ile Asn Gln Arg Ser Phe Leu Val Ser
                115                 120                 125

Gly Leu Gly Gly Glu His Thr Ala Phe Asn Gln Leu Pro Ser Gly Lys
        130                 135                 140

Ala Glu Tyr His Gly Lys Ala Phe Ser Ser Asp Asp Ala Gly Gly Lys
145                 150                 155                 160

Leu Thr Tyr Thr Ile Asp Phe Ala Ala Lys Gln Gly His Gly Lys Ile
                165                 170                 175

Glu His Leu Lys Thr Pro Glu Gln Asn Val Glu Leu Ala Ser Ala Glu
                180                 185                 190

Leu Lys Ala Asp Glu Lys Ser His Ala Val Ile Leu Gly Asp Thr Arg
                195                 200                 205

Tyr Gly Ser Glu Glu Lys Gly Thr Tyr His Leu Ala Leu Phe Gly Asp
        210                 215                 220

Arg Ala Gln Glu Ile Ala Gly Ser Ala Thr Val Lys Ile Arg Glu Lys
225                 230                 235                 240

Val His Glu Ile Gly Ile Ala Gly Lys Gln
                245                 250
```

<210> SEQ ID NO 7
<211> LENGTH: 792
<212> TYPE: PRT
<213> ORGANISM: Neisseria meningitidis

<400> SEQUENCE: 7

```
Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
                20                  25                  30

Pro Val Lys Ala Glu Ile Lys Ala Val Arg Val Lys Gly Gln Arg Asn
                35                  40                  45
```

```
Ala Pro Ala Ala Val Glu Arg Val Asn Leu Asn Arg Ile Lys Gln Glu
         50                  55                  60

Met Ile Arg Asp Asn Lys Asp Leu Val Arg Tyr Ser Thr Asp Val Gly
 65                  70                  75                  80

Leu Ser Asp Ser Gly Arg His Gln Lys Gly Phe Ala Val Arg Gly Val
                 85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
            115                 120                 125

Arg Leu Ser Ile Asp Pro Glu Leu Val Arg Asn Ile Glu Ile Val Lys
130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Asp Asp Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Asn
210                 215                 220

Arg Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr Asn His His
                245                 250                 255

Ala Leu Gly Lys Ile Ala Tyr Gln Ile Asn Asp Asn His Arg Ile Gly
            260                 265                 270

Ala Ser Leu Asn Gly Gln Gln Gly His Asn Tyr Thr Val Glu Glu Ser
            275                 280                 285

Tyr Asn Leu Thr Ala Ser Ser Trp Arg Glu Ala Asp Asp Val Asn Arg
290                 295                 300

Arg Arg Asn Ala Asn Leu Phe Tyr Glu Trp Met Pro Asp Ser Asn Trp
305                 310                 315                 320

Leu Ser Ser Leu Lys Ala Asp Phe Asp Tyr Gln Lys Thr Lys Val Ala
                325                 330                 335

Ala Val Asn Asn Lys Gly Ser Phe Pro Met Asp Tyr Ser Thr Trp Thr
            340                 345                 350

Arg Asn Tyr Asn Gln Lys Asp Leu Asp Glu Ile Tyr Asn Arg Ser Met
            355                 360                 365

Asp Thr Arg Phe Lys Arg Phe Thr Leu Arg Leu Asp Ser His Pro Leu
370                 375                 380

Gln Leu Gly Gly Gly Arg His Arg Leu Ser Phe Lys Thr Phe Val Ser
385                 390                 395                 400

Arg Arg Asp Phe Glu Asn Leu Asn Arg Asp Asp Tyr Tyr Phe Ser Gly
                405                 410                 415

Arg Val Val Arg Thr Thr Ser Ser Ile Gln His Pro Val Lys Thr Thr
            420                 425                 430

Asn Tyr Gly Phe Ser Leu Ser Asp Gln Ile Gln Trp Asn Asp Val Phe
            435                 440                 445

Ser Ser Arg Ala Gly Ile Arg Tyr Asp His Thr Lys Met Thr Pro Gln
450                 455                 460
```

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
            485                 490                 495

Asn Gln Ala Trp Arg Val Gly Tyr Asp Ile Thr Ser Gly Tyr Arg Val
        500                 505                 510

Pro Asn Ala Ser Glu Val Tyr Phe Thr Tyr Asn His Gly Ser Gly Asn
        515                 520                 525

Trp Leu Pro Asn Pro Asn Leu Lys Ala Glu Arg Ser Thr Thr His Thr
    530                 535                 540

Leu Ser Leu Gln Gly Arg Ser Glu Lys Gly Met Leu Asp Ala Asn Leu
545                 550                 555                 560

Tyr Gln Ser Asn Tyr Arg Asn Phe Leu Ser Glu Gln Lys Leu Thr
                565                 570                 575

Thr Ser Gly Thr Pro Gly Cys Thr Glu Glu Asn Ala Tyr Tyr Gly Ile
            580                 585                 590

Cys Ser Asp Pro Tyr Lys Glu Lys Leu Asp Trp Gln Met Lys Asn Ile
        595                 600                 605

Asp Lys Ala Arg Ile Arg Gly Ile Glu Leu Thr Gly Arg Leu Asn Val
    610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
            660                 665                 670

Glu Lys Trp Gly Val Phe Ser Arg Leu Thr Tyr Leu Gly Ala Lys Lys
        675                 680                 685

Val Lys Asp Ala Gln Tyr Thr Val Tyr Glu Asn Lys Gly Trp Gly Thr
    690                 695                 700

Pro Leu Gln Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
            740                 745                 750

Asp Ser Leu Arg Gly Leu Tyr Ser Tyr Ser Thr Thr Asn Ala Val Asp
        755                 760                 765

Arg Asp Gly Lys Gly Leu Asp Arg Tyr Arg Ala Pro Gly Arg Asn Tyr
    770                 775                 780

Ala Val Ser Leu Glu Trp Lys Phe
785                 790

<210> SEQ ID NO 8
<211> LENGTH: 793
<212> TYPE: PRT
<213> ORGANISM: Neisseria meningitidis

<400> SEQUENCE: 8

Met Lys Pro Leu Gln Met Leu Pro Ile Ala Ala Leu Val Gly Ser Ile
1               5                   10                  15

Phe Gly Asn Pro Val Phe Ala Ala Asp Glu Ala Thr Glu Thr Thr
                20                  25                  30

Pro Val Lys Ala Glu Val Lys Ala Val Arg Val Lys Gly Gln Arg Asn
            35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Asp Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Pro Glu Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Lys
    210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr Asn His His
                245                 250                 255

Ala Leu Gly Lys Ile Ala Tyr Gln Ile Asn Asp Asn His Arg Ile Gly
            260                 265                 270

Ala Ser Leu Asn Gly Gln Gln Gly His Asn Tyr Thr Val Glu Glu Ser
        275                 280                 285

Tyr Asn Leu Leu Ala Ser Tyr Trp Arg Glu Ala Asp Asp Val Asn Arg
    290                 295                 300

Arg Arg Asn Thr Asn Leu Phe Tyr Glu Trp Thr Pro Glu Ser Asp Arg
305                 310                 315                 320

Leu Ser Met Val Lys Ala Asp Val Asp Tyr Gln Lys Thr Lys Val Ser
                325                 330                 335

Ala Val Asn Tyr Lys Gly Ser Phe Pro Ile Glu Asp Ser Ser Thr Leu
            340                 345                 350

Thr Arg Asn Tyr Asn Gln Lys Asp Leu Asp Glu Ile Tyr Asn Arg Ser
        355                 360                 365

Met Asp Thr Arg Phe Lys Arg Ile Thr Leu Arg Leu Asp Ser His Pro
    370                 375                 380

Leu Gln Leu Gly Gly Gly Arg His Arg Leu Ser Phe Lys Thr Phe Ala
385                 390                 395                 400

Ser Arg Arg Asp Phe Glu Asn Leu Asn Arg Asp Asp Tyr Tyr Phe Ser
                405                 410                 415

Gly Arg Val Val Arg Thr Thr Ser Ser Ile Gln His Pro Val Lys Thr
            420                 425                 430

Thr Asn Tyr Gly Phe Ser Leu Ser Asp Gln Ile Gln Trp Asn Asp Val
        435                 440                 445

Phe Ser Ser Arg Ala Gly Ile Arg Tyr Asp His Thr Lys Met Thr Pro
    450                 455                 460

```
Gln Glu Leu Asn Ala Glu Cys His Ala Cys Asp Lys Thr Pro Pro Ala
465                 470                 475                 480

Ala Asn Thr Tyr Lys Gly Trp Ser Gly Phe Val Gly Leu Ala Ala Gln
            485                 490                 495

Leu Asn Gln Ala Trp Arg Val Gly Tyr Asp Ile Thr Ser Gly Tyr Arg
        500                 505                 510

Val Pro Asn Ala Ser Glu Val Tyr Phe Thr Tyr Asn His Gly Ser Gly
    515                 520                 525

Asn Trp Leu Pro Asn Pro Asn Leu Lys Ala Glu Arg Thr Thr Thr His
530                 535                 540

Thr Leu Ser Leu Gln Gly Arg Ser Glu Lys Gly Thr Leu Asp Ala Asn
545                 550                 555                 560

Leu Tyr Gln Ser Asn Tyr Arg Asn Phe Leu Ser Glu Glu Gln Lys Leu
                565                 570                 575

Thr Thr Ser Gly Asp Val Ser Cys Thr Gln Met Asn Tyr Tyr Tyr Gly
            580                 585                 590

Met Cys Ser Asn Pro Tyr Ser Glu Lys Leu Glu Trp Gln Met Gln Asn
        595                 600                 605

Ile Asp Lys Ala Arg Ile Arg Gly Ile Glu Leu Thr Gly Arg Leu Asn
    610                 615                 620

Val Asp Lys Val Ala Ser Phe Val Pro Glu Gly Trp Lys Leu Phe Gly
625                 630                 635                 640

Ser Leu Gly Tyr Ala Lys Ser Lys Leu Ser Gly Asp Asn Ser Leu Leu
                645                 650                 655

Ser Thr Gln Pro Leu Lys Val Ile Ala Gly Ile Asp Tyr Glu Ser Pro
            660                 665                 670

Ser Glu Lys Trp Gly Val Phe Ser Arg Leu Thr Tyr Leu Gly Ala Lys
        675                 680                 685

Lys Val Lys Asp Ala Gln Tyr Thr Val Tyr Glu Asn Lys Gly Trp Gly
    690                 695                 700

Thr Pro Leu Gln Lys Lys Val Lys Asp Tyr Pro Trp Leu Asn Lys Ser
705                 710                 715                 720

Ala Tyr Val Phe Asp Met Tyr Gly Phe Tyr Lys Pro Val Lys Asn Leu
                725                 730                 735

Thr Leu Arg Ala Gly Val Tyr Asn Val Phe Asn Arg Lys Tyr Thr Thr
            740                 745                 750

Trp Asp Ser Leu Arg Gly Leu Tyr Ser Tyr Ser Thr Thr Asn Ser Val
        755                 760                 765

Asp Arg Asp Gly Lys Gly Leu Asp Arg Tyr Arg Ala Pro Ser Arg Asn
    770                 775                 780

Tyr Ala Val Ser Leu Glu Trp Lys Phe
785                 790

<210> SEQ ID NO 9
<211> LENGTH: 488
<212> TYPE: PRT
<213> ORGANISM: Neisseria meningitidis

<400> SEQUENCE: 9

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
            35                  40                  45
```

```
Ala Lys Glu Asp Ala Pro Gln Ala Gly Ser Gln Gly Gln Gly Ala Pro
     50                  55                  60

Ser Ala Gln Gly Ser Gln Asp Met Ala Ala Val Ser Glu Glu Asn Thr
 65                  70                  75                  80

Gly Asn Gly Gly Ala Val Thr Ala Asp Asn Pro Lys Asn Glu Asp Glu
                     85                  90                  95

Val Ala Gln Asn Asp Met Pro Gln Asn Ala Ala Gly Thr Asp Ser Ser
                100                 105                 110

Thr Pro Asn His Thr Pro Asp Pro Asn Met Leu Ala Gly Asn Met Glu
             115                 120                 125

Asn Gln Ala Thr Asp Ala Gly Glu Ser Ser Gln Pro Ala Asn Gln Pro
        130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460
```

```
Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 10
<211> LENGTH: 364
<212> TYPE: PRT
<213> ORGANISM: Neisseria meningitidis

<400> SEQUENCE: 10

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
                20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
        50                  55                  60

Asp Gly Thr Ile Thr Gln Lys Asp Ala Thr Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350
```

Ser Ala Ala Tyr His Val Gly Val Asn Tyr Glu Trp
        355                 360

<210> SEQ ID NO 11
<211> LENGTH: 174
<212> TYPE: PRT
<213> ORGANISM: Neisseria meningitidis

<400> SEQUENCE: 11

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
            20                  25                  30

His Ala Lys Ala Ser Ser Leu Gly Ser Ala Lys Gly Phe Ser Pro
        35                  40                  45

Arg Ile Ser Ala Gly Tyr Arg Ile Asn Asp Leu Arg Phe Ala Val Asp
    50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
    130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170

<210> SEQ ID NO 12
<211> LENGTH: 591
<212> TYPE: PRT
<213> ORGANISM: Neisseria meningitidis

<400> SEQUENCE: 12

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

```
Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
            165                 170                 175

Val His Leu Asn Gly Ile Gly Ser Thr Leu Thr Asp Thr Leu Leu Asn
        180                 185                 190

Thr Gly Ala Thr Thr Asn Val Thr Asn Asp Asn Val Thr Asp Asp Glu
    195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
            245                 250                 255

Thr Thr Val Asn Val Glu Ser Lys Asp Asn Gly Lys Lys Thr Glu Val
        260                 265                 270

Lys Ile Gly Ala Lys Thr Ser Val Ile Lys Glu Lys Asp Gly Lys Leu
    275                 280                 285

Val Thr Gly Lys Asp Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
            325                 330                 335

Asp Lys Phe Glu Thr Val Thr Ser Gly Thr Asn Val Thr Phe Ala Ser
        340                 345                 350

Gly Lys Gly Thr Thr Ala Thr Val Ser Lys Asp Asp Gln Gly Asn Ile
    355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Thr Arg
        420                 425                 430

Asn Gly Lys Asn Ile Asp Ile Ala Thr Ser Met Thr Pro Gln Phe Ser
    435                 440                 445

Ser Val Ser Leu Gly Ala Gly Ala Asp Ala Pro Thr Leu Ser Val Asp
450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
            485                 490                 495

Ala Gln Leu Lys Gly Val Ala Gln Asn Leu Asn Asn Arg Ile Asp Asn
        500                 505                 510

Val Asp Gly Asn Ala Arg Ala Gly Ile Ala Gln Ala Ile Ala Thr Ala
    515                 520                 525

Gly Leu Val Gln Ala Tyr Leu Pro Gly Lys Ser Met Met Ala Ile Gly
530                 535                 540

Gly Gly Thr Tyr Arg Gly Glu Ala Gly Tyr Ala Ile Gly Tyr Ser Ser
545                 550                 555                 560
```

-continued

```
Ile Ser Asp Gly Gly Asn Trp Ile Ile Lys Gly Thr Ala Ser Gly Asn
                565                 570                 575
Ser Arg Gly His Phe Gly Ala Ser Ala Ser Val Gly Tyr Gln Trp
            580                 585                 590

<210> SEQ ID NO 13
<211> LENGTH: 1457
<212> TYPE: PRT
<213> ORGANISM: Neisseria meningitidis

<400> SEQUENCE: 13

Met Lys Thr Thr Asp Lys Arg Thr Thr Glu Thr His Arg Lys Ala Pro
1               5                   10                  15
Lys Thr Gly Arg Ile Arg Phe Ser Pro Ala Tyr Leu Ala Ile Cys Leu
                20                  25                  30
Ser Phe Gly Ile Leu Pro Gln Ala Trp Ala Gly His Thr Tyr Phe Gly
            35                  40                  45
Ile Asn Tyr Gln Tyr Tyr Arg Asp Phe Ala Glu Asn Lys Gly Lys Phe
        50                  55                  60
Ala Val Gly Ala Lys Asp Ile Glu Val Tyr Asn Lys Lys Gly Glu Leu
65                  70                  75                  80
Val Gly Lys Ser Met Thr Lys Ala Pro Met Ile Asp Phe Ser Val Val
                85                  90                  95
Ser Arg Asn Gly Val Ala Ala Leu Val Gly Asp Gln Tyr Ile Val Ser
                100                 105                 110
Val Ala His Asn Gly Gly Tyr Asn Asn Val Asp Phe Gly Ala Glu Gly
            115                 120                 125
Arg Asn Pro Asp Gln His Arg Phe Thr Tyr Lys Ile Val Lys Arg Asn
        130                 135                 140
Asn Tyr Lys Ala Gly Thr Lys Gly His Pro Tyr Gly Gly Asp Tyr His
145                 150                 155                 160
Met Pro Arg Leu His Lys Phe Val Thr Asp Ala Glu Pro Val Glu Met
                165                 170                 175
Thr Ser Tyr Met Asp Gly Arg Lys Tyr Ile Asp Gln Asn Asn Tyr Pro
                180                 185                 190
Asp Arg Val Arg Ile Gly Ala Gly Arg Gln Tyr Trp Arg Ser Asp Glu
            195                 200                 205
Asp Glu Pro Asn Asn Arg Glu Ser Ser Tyr His Ile Ala Ser Ala Tyr
        210                 215                 220
Ser Trp Leu Val Gly Gly Asn Thr Phe Ala Gln Asn Gly Ser Gly Gly
225                 230                 235                 240
Gly Thr Val Asn Leu Gly Ser Glu Lys Ile Lys His Ser Pro Tyr Gly
                245                 250                 255
Phe Leu Pro Thr Gly Gly Ser Phe Gly Asp Ser Gly Ser Pro Met Phe
                260                 265                 270
Ile Tyr Asp Ala Gln Lys Gln Lys Trp Leu Ile Asn Gly Val Leu Gln
            275                 280                 285
Thr Gly Asn Pro Tyr Ile Gly Lys Ser Asn Gly Phe Gln Leu Val Arg
        290                 295                 300
Lys Asp Trp Phe Tyr Asp Glu Ile Phe Ala Gly Asp Thr His Ser Val
305                 310                 315                 320
Phe Tyr Glu Pro Arg Gln Asn Gly Lys Tyr Ser Phe Asn Asp Asp Asn
                325                 330                 335
Asn Gly Thr Gly Lys Ile Asn Ala Lys His Glu His Asn Ser Leu Pro
                340                 345                 350
```

```
Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
    690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
        755                 760                 765
```

-continued

```
Asn Leu Thr Gly Leu Ala Thr Leu Asn Gly Asn Leu Ser Ala Asn Gly
    770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
                820                 825                 830

Ala Val Gln Asn Gly Ser Leu Thr Leu Ser Gly Asn Ala Lys Ala Asn
                835                 840                 845

Val Ser His Ser Ala Leu Asn Gly Asn Val Ser Leu Ala Asp Lys Ala
850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
                900                 905                 910

Asn Ser Ala Tyr Arg His Asp Ala Ala Gly Ala Gln Thr Gly Ser Ala
                915                 920                 925

Thr Asp Ala Pro Arg Arg Ser Arg Arg Ser Arg Arg Ser Leu Leu
                930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
                980                 985                 990

Gly Thr Tyr Thr Leu Ala Val Asn Asn Thr Gly Asn Glu Pro Ala Ser
                995                 1000                1005

Leu Glu Gln Leu Thr Val Val Glu Gly Lys Asp Asn Lys Pro Leu Ser
    1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala
                1060                1065                1070

Lys Lys Gln Ala Glu Lys Asp Asn Ala Gln Ser Leu Asp Ala Leu Ile
    1075                1080                1085

Ala Ala Gly Arg Asp Ala Val Glu Lys Thr Glu Ser Val Ala Glu Pro
    1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
                1125                1130                1135

Arg Glu Ala Glu Thr Arg Pro Ala Thr Thr Ala Phe Pro Arg Ala Arg
                1140                1145                1150

Arg Ala Arg Arg Asp Leu Pro Gln Leu Gln Pro Gln Pro Gln Pro Gln
    1155                1160                1165

Pro Gln Arg Asp Leu Ile Ser Arg Tyr Ala Asn Ser Gly Leu Ser Glu
    1170                1175                1180

Phe Ser Ala Thr Leu Asn Ser Val Phe Ala Val Gln Asp Glu Leu Asp
```

```
                    1185               1190               1195               1200
       Arg Val Phe Ala Glu Asp Arg Asn Ala Val Trp Thr Ser Gly Ile
                        1205               1210               1215

Arg Asp Thr Lys His Tyr Arg Ser Gln Asp Phe Arg Ala Tyr Arg Gln
                        1220               1225               1230

Gln Thr Asp Leu Arg Gln Ile Gly Met Gln Lys Asn Leu Gly Ser Gly
                        1235               1240               1245

Arg Val Gly Ile Leu Phe Ser His Asn Arg Thr Glu Asn Thr Phe Asp
                        1250               1255               1260

Asp Gly Ile Gly Asn Ser Ala Arg Leu Ala His Gly Ala Val Phe Gly
       1265               1270               1275               1280

Gln Tyr Gly Ile Asp Arg Phe Tyr Ile Gly Ile Ser Ala Gly Ala Gly
                        1285               1290               1295

Phe Ser Gly Ser Leu Ser Asp Gly Ile Gly Gly Lys Ile Arg Arg
                        1300               1305               1310

Arg Val Leu His Tyr Gly Ile Gln Ala Arg Tyr Arg Ala Gly Phe Gly
                        1315               1320               1325

Gly Phe Gly Ile Glu Pro His Ile Gly Ala Thr Arg Tyr Phe Val Gln
                        1330               1335               1340

Lys Ala Asp Tyr Arg Tyr Glu Asn Val Asn Ile Ala Thr Pro Gly Leu
       1345               1350               1355               1360

Ala Phe Asn Arg Tyr Arg Ala Gly Ile Lys Ala Asp Tyr Ser Phe Lys
                        1365               1370               1375

Pro Ala Gln His Ile Ser Ile Thr Pro Tyr Leu Ser Leu Ser Tyr Thr
                        1380               1385               1390

Asp Ala Ala Ser Gly Lys Val Arg Thr Arg Val Asn Thr Ala Val Leu
                        1395               1400               1405

Ala Gln Asp Phe Gly Lys Thr Arg Ser Ala Glu Trp Gly Val Asn Ala
                        1410               1415               1420

Glu Ile Lys Gly Phe Thr Leu Ser Leu His Ala Ala Ala Lys Gly
       1425               1430               1435               1440

Pro Gln Leu Glu Ala Gln His Ser Ala Gly Ile Lys Leu Gly Tyr Arg
                        1445               1450               1455

Trp

<210> SEQ ID NO 14
<211> LENGTH: 797
<212> TYPE: PRT
<213> ORGANISM: Neisseria meningitidis

<400> SEQUENCE: 14

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
                20                  25                  30

Leu Gln Arg Thr Glu Pro Ser Val Phe Asn Tyr Leu Pro Val Lys
            35                  40                  45

Val Gly Asp Thr Tyr Asn Asp Thr His Gly Ser Ala Ile Ile Lys Ser
        50                  55                  60

Leu Tyr Ala Thr Gly Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
```

```
              100                 105                 110
Leu Glu Ser Phe Gly Leu Ala Gln Ser Gln Tyr Phe Asn Gln Ala Thr
              115                 120                 125
Leu Asn Gln Ala Val Ala Gly Leu Lys Glu Glu Tyr Leu Gly Arg Gly
              130                 135             140
Lys Leu Asn Ile Gln Ile Thr Pro Lys Val Thr Lys Leu Ala Arg Asn
145                 150                 155                 160
Arg Val Asp Ile Asp Ile Thr Ile Asp Glu Gly Lys Ser Ala Lys Ile
                  165                 170                 175
Thr Asp Ile Glu Phe Glu Gly Asn Gln Val Tyr Ser Asp Arg Lys Leu
                  180                 185                 190
Met Arg Gln Met Ser Leu Thr Glu Gly Gly Ile Trp Thr Trp Leu Thr
                  195                 200                 205
Arg Ser Asn Gln Phe Asn Glu Gln Lys Phe Ala Gln Asp Met Glu Lys
                  210                 215                 220
Val Thr Asp Phe Tyr Gln Asn Asn Gly Tyr Phe Asp Phe Arg Ile Leu
225                 230                 235                 240
Asp Thr Asp Ile Gln Thr Asn Glu Asp Lys Thr Lys Gln Thr Ile Lys
                  245                 250                 255
Ile Thr Val His Glu Gly Gly Arg Phe Arg Trp Gly Lys Val Ser Ile
                  260                 265                 270
Glu Gly Asp Thr Asn Glu Val Pro Lys Ala Glu Leu Glu Lys Leu Leu
                  275                 280                 285
Thr Met Lys Pro Gly Lys Trp Tyr Glu Arg Gln Gln Met Thr Ala Val
                  290                 295                 300
Leu Gly Glu Ile Gln Asn Arg Met Gly Ser Ala Gly Tyr Ala Tyr Ser
305                 310                 315                 320
Glu Ile Ser Val Gln Pro Leu Pro Asn Ala Glu Thr Lys Thr Val Asp
                  325                 330                 335
Phe Val Leu His Ile Glu Pro Gly Arg Lys Ile Tyr Val Asn Glu Ile
                  340                 345                 350
His Ile Thr Gly Asn Asn Lys Thr Arg Asp Glu Val Val Arg Arg Glu
                  355                 360                 365
Leu Arg Gln Met Glu Ser Ala Pro Tyr Asp Thr Ser Lys Leu Gln Arg
                  370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                  405                 410                 415
Ser Leu Thr Glu Arg Ser Thr Gly Ser Leu Asp Leu Ser Ala Gly Trp
                  420                 425                 430
Val Gln Asp Thr Gly Leu Val Met Ser Ala Gly Val Ser Gln Asp Asn
                  435                 440                 445
Leu Phe Gly Thr Gly Lys Ser Ala Ala Leu Arg Ala Ser Arg Ser Lys
                  450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Val Tyr Gly Lys Ala Phe Asp Pro
                  485                 490                 495
Arg Lys Ala Ser Thr Ser Ile Lys Gln Tyr Lys Thr Thr Thr Ala Gly
                  500                 505                 510
Ala Gly Ile Arg Met Ser Val Pro Val Thr Glu Tyr Asp Arg Val Asn
                  515                 520                 525
```

-continued

Phe Gly Leu Val Ala Glu His Leu Thr Val Asn Thr Tyr Asn Lys Ala
            530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
            595                 600                 605

Tyr Ser Ala Thr His Asn Gln Thr Trp Phe Phe Pro Leu Ser Lys Thr
            610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
            675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ser Ala Thr Gly Gly Arg Val Gln
                725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
            755                 760                 765

Pro Met Lys Phe Ser Tyr Ala Tyr Pro Leu Lys Lys Lys Pro Glu Asp
770                 775                 780

Glu Ile Gln Arg Phe Gln Phe Gln Leu Gly Thr Thr Phe
785                 790                 795

<210> SEQ ID NO 15
<211> LENGTH: 6
<212> TYPE: PRT
<213> ORGANISM: Artificial Sequence
<220> FEATURE:
<223> OTHER INFORMATION: Linker peptide

<400> SEQUENCE: 15

Gly Ser Gly Gly Gly Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Linker peptide

<400> SEQUENCE: 16

Gly Ser Gly Ser Gly Gly Gly Gly
1               5

```
<210> SEQ ID NO 17
<211> LENGTH: 6
<212> TYPE: PRT
<213> ORGANISM: Artificial Sequence
<220> FEATURE:
<223> OTHER INFORMATION: Hexa-histidine tag

<400> SEQUENCE: 17

His His His His His His
1               5

<210> SEQ ID NO 18
<211> LENGTH: 26
<212> TYPE: DNA
<213> ORGANISM: Artificial Sequence
<220> FEATURE:
<223> OTHER INFORMATION: Immunostimulatory oligonucleotide
<220> FEATURE:
<221> NAME/KEY: n
<222> LOCATION: 1,3,5,7,9,11,13,15,17,19,21,23,25
<223> OTHER INFORMATION: 'n' is Inosine

<400> SEQUENCE: 18
ncncncncnc ncncncncnc ncncnc                                          26

<210> SEQ ID NO 19
<211> LENGTH: 11
<212> TYPE: PRT
<213> ORGANISM: Artificial Sequence
<220> FEATURE:
<223> OTHER INFORMATION: Polycationic peptide

<400> SEQUENCE: 19

Lys Leu Lys Leu Leu Leu Leu Leu Lys Leu Lys
1               5                   10

<210> SEQ ID NO 20
<211> LENGTH: 274
<212> TYPE: PRT
<213> ORGANISM: Neisseria meningitidis

<400> SEQUENCE: 20

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160
```

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 21
<211> LENGTH: 273
<212> TYPE: PRT
<213> ORGANISM: Neisseria meningitidis

<400> SEQUENCE: 21

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

```
Thr Val Lys Ile Gly Glu Lys Val His Glu Ile Gly Ile Ala Gly Lys
            260                 265                 270
Gln

<210> SEQ ID NO 22
<211> LENGTH: 281
<212> TYPE: PRT
<213> ORGANISM: Neisseria meningitidis

<400> SEQUENCE: 22

Met Asn Arg Thr Ala Phe Cys Cys Leu Ser Leu Thr Ala Leu Ile
1               5                   10                  15

Leu Thr Ala Cys Ser Ser Gly Gly Gly Ser Gly Gly Gly Val
            20                  25                  30

Ala Ala Asp Ile Gly Thr Gly Leu Ala Asp Ala Leu Thr Ala Pro Leu
            35                  40                  45

Asp His Lys Asp Lys Gly Leu Lys Ser Leu Thr Leu Glu Asp Ser Ile
        50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280

<210> SEQ ID NO 23
<211> LENGTH: 260
<212> TYPE: PRT
<213> ORGANISM: Neisseria meningitidis

<400> SEQUENCE: 23

Cys Ser Ser Gly Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
```

```
                    20                  25                  30
Asp Lys Gly Leu Lys Ser Leu Thr Leu Glu Asp Ser Ile Ser Gln Asn
            35                  40                  45
Gly Thr Leu Thr Leu Ser Ala Gln Gly Ala Glu Lys Thr Tyr Gly Asn
        50                  55                  60
Gly Asp Ser Leu Asn Thr Gly Lys Leu Lys Asn Asp Lys Val Ser Arg
65                  70                  75                  80
Phe Asp Phe Ile Arg Gln Ile Glu Val Asp Gly Gln Leu Ile Thr Leu
                85                  90                  95
Glu Ser Gly Glu Phe Gln Val Tyr Lys Gln Ser His Ser Ala Leu Thr
            100                 105                 110
Ala Leu Gln Thr Glu Gln Glu Gln Asp Pro Glu His Ser Glu Lys Met
        115                 120                 125
Val Ala Lys Arg Arg Phe Arg Ile Gly Asp Ile Ala Gly Glu His Thr
    130                 135                 140
Ser Phe Asp Lys Leu Pro Lys Asp Val Met Ala Thr Tyr Arg Gly Thr
145                 150                 155                 160
Ala Phe Gly Ser Asp Ala Gly Gly Lys Leu Thr Tyr Thr Ile Asp
                165                 170                 175
Phe Ala Ala Lys Gln Gly His Gly Lys Ile Glu His Leu Lys Ser Pro
            180                 185                 190
Glu Leu Asn Val Asp Leu Ala Val Ala Tyr Ile Lys Pro Asp Glu Lys
        195                 200                 205
His His Ala Val Ile Ser Gly Ser Val Leu Tyr Asn Gln Asp Glu Lys
    210                 215                 220
Gly Ser Tyr Ser Leu Gly Ile Phe Gly Glu Lys Ala Gln Glu Val Ala
225                 230                 235                 240
Gly Ser Ala Glu Val Glu Thr Ala Asn Gly Ile His His Ile Gly Leu
                245                 250                 255
Ala Ala Lys Gln
            260

<210> SEQ ID NO 24
<211> LENGTH: 262
<212> TYPE: PRT
<213> ORGANISM: Neisseria meningitidis

<400> SEQUENCE: 24

Cys Ser Ser Gly Gly Gly Ser Gly Gly Gly Val Ala Ala Asp
1               5                   10                  15
Ile Gly Ala Gly Leu Ala Asp Ala Leu Thr Ala Pro Leu Asp His Lys
                20                  25                  30
Asp Lys Gly Leu Lys Ser Leu Thr Leu Glu Asp Ser Ile Ser Gln Asn
            35                  40                  45
Gly Thr Leu Thr Leu Ser Ala Gln Gly Ala Glu Arg Thr Phe Lys Ala
        50                  55                  60
Gly Asp Lys Asp Asn Ser Leu Asn Thr Gly Lys Leu Lys Asn Asp Lys
65                  70                  75                  80
Ile Ser Arg Phe Asp Phe Ile Arg Gln Ile Glu Val Asp Gly Gln Leu
                85                  90                  95
Ile Thr Leu Glu Ser Gly Glu Phe Gln Val Tyr Lys Gln Ser His Ser
            100                 105                 110
Ala Leu Thr Ala Leu Gln Thr Glu Gln Val Gln Asp Ser Glu His Ser
        115                 120                 125
```

```
Gly Lys Met Val Ala Lys Arg Gln Phe Arg Ile Gly Asp Ile Val Gly
            130                 135                 140

Glu His Thr Ser Phe Asp Lys Leu Pro Lys Asp Val Met Ala Thr Tyr
145                 150                 155                 160

Arg Gly Thr Ala Phe Gly Ser Asp Ala Gly Gly Lys Leu Thr Tyr
                165                 170                 175

Thr Ile Asp Ala Ala Lys Gln Gly His Gly Lys Ile Glu His Leu Lys
            180                 185                 190

Ser Pro Glu Leu Asn Val Asp Leu Ala Ala Asp Ile Lys Pro Asp
            195                 200                 205

Glu Lys His His Ala Val Ile Ser Gly Ser Val Leu Tyr Asn Gln Ala
210                 215                 220

Glu Lys Gly Ser Tyr Ser Leu Gly Ile Phe Gly Gln Ala Gln Glu
225                 230                 235                 240

Val Ala Gly Ser Ala Glu Val Glu Thr Ala Asn Gly Ile Arg His Ile
                245                 250                 255

Gly Leu Ala Ala Lys Gln
            260

<210> SEQ ID NO 25
<211> LENGTH: 261
<212> TYPE: PRT
<213> ORGANISM: Neisseria meningitidis

<400> SEQUENCE: 25

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Lys Thr Phe Lys Val Gly
50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
            115                 120                 125

Ser Leu Ile Asn Gln Arg Ser Phe Leu Val Ser Gly Leu Gly Gly Glu
130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
            195                 200                 205

Lys Ser His Ala Val Ile Leu Gly Asp Thr Arg Tyr Gly Ser Glu Glu
210                 215                 220

Lys Gly Thr Tyr His Leu Ala Leu Phe Gly Asp Arg Ala Gln Glu Ile
225                 230                 235                 240
```

```
Ala Gly Ser Ala Thr Val Lys Ile Arg Glu Lys Val His Glu Ile Gly
            245                 250                 255
Ile Ala Gly Lys Gln
        260
```

ADJUVANTING MENINGOCOCCAL FACTOR H BINDING PROTEIN

CROSS REFERENCE TO RELATED APPLICATIONS

This application is a Continuation of U.S. patent application Ser. No. 15/604,054, filed May 24, 2017, now U.S. Pat. No. 10,245,311; which is a Continuation of U.S. patent application Ser. No. 15/393,092, filed Dec. 28, 2016; which is a Divisional of U.S. patent application Ser. No. 14/307,001, filed Jun. 17, 2014, now U.S. Pat. No. 9,572,884; which is a Continuation of U.S. patent application Ser. No. 13/767,853, filed Feb. 14, 2013, now U.S. Pat. No. 8,834,888; which is a Continuation of U.S. patent application Ser. No. 13/403,865, filed Feb. 23, 2012, now U.S. Pat. No. 8,398,988; which is a Continuation of U.S. patent application Ser. No. 13/260,534, claiming an international filing date of Mar. 24, 2010; which is the National Stage of International Patent Application No. PCT/IB2010/000733, filed Mar. 24, 2010; which claims the benefit of U.S. Provisional Patent Application No. 61/162,999, filed Mar. 24, 2009, the disclosures of which are herein incorporated by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 303822003105SEQLIST.TXT, date recorded: Feb. 5, 2019, size: 74 KB).

TECHNICAL FIELD

This invention is in the field of meningococcal vaccines, in particular those containing fHBP antigen.

BACKGROUND ART

*Neisseria meningitidis* (meningococcus) is a Gram-negative spherical bacterium. Current meningococcal vaccines are also based on capsular saccharides. These include monovalent serogroup C conjugate vaccines and 4-valent conjugate mixtures for serogroups A, C, W135 and Y. There is currently no useful vaccine authorised for general use against serogroup B ('MenB').

One antigen which has been proposed for use in immunising against MenB is the factor H binding protein (fHBP). This antigen has also been called protein '741' (SEQ IDs 2535 & 2536 in ref. 34), 'NMB1870', 'GNA1870' [refs. 1-3], 'P2086', 'LP2086' or 'ORF2086' [4-6]. The protein has been well studied. It is naturally a lipoprotein and is expressed across all meningococcal serogroups. The structure of fHbp's C-terminal immunodominant domain ('fHbpC') has been determined by NMR [7]. This part of the protein forms an eight-stranded β-barrel, whose strands are connected by loops of variable lengths. The barrel is preceded by a short α-helix and by a flexible N-terminal tail.

The fHBP antigen fails into three distinct variants [8] and it has been found that serum raised against a given family is bactericidal within the same family, but is not active against strains which express one of the other two families i.e. there is intra-family cross-protection, but not inter-family cross-protection. Thus reference 8 proposes to combine different variants of fHBP into a single vaccine composition, thereby increasing strain coverage, either as a mixture of separate proteins or as a fusion protein of the different variants (the latter being 'tandem proteins').

Reference 9 also reports a fHBP tandem protein (pages 18-19 of reference 9). This tandem protein was purified and mixed with aluminium phosphate as an adjuvant, but it is reported not to adsorb well to the adjuvant. Good adsorption of the antigens is desirable, and it has been found that such mixed fHBP proteins readily adsorb if aluminium hydroxide is used as an adjuvant instead. A problem when using aluminium hydroxide as an adjuvant, however, is that it can degrade certain antigens. For instance, reference 10 reports that it can hydrolyse *H. influenzae* type B conjugate vaccines, even at low temperatures, thus leading to reduced efficacy. Similarly, hydrolysis of *S. typhi* Vi capsular saccharide in the presence of aluminium hydroxide is reported in reference 11. Thus it can be desirable to formulate antigens using an adjuvant based on aluminium phosphate, particularly if the adjuvanted vaccine may be mixed (either during manufacture or at the time of use) with an antigen that may be susceptible to damage by an aluminium hydroxide e.g. a conjugated bacterial capsular saccharide.

Thus there Is a need to provide formulations of fHBP, and in particular of multiple fHBP variants, in which the fHBP(s) is/are adsorbed to an adjuvant but which do not require aluminium hydroxide.

DISCLOSURE OF THE INVENTION

The inventors have identified general techniques for achieving efficient adsorption of fHBP proteins to aluminium hydroxyphosphate adjuvants. The use of aluminium hvdroxyphosphate can avoid the need to use aluminium hydroxide, and the inventors' techniques avoid the inefficient adsorption described in reference 9. The adsorption techniques are particularly useful for compositions which include multiple fHBP variants.

In a first aspect of the invention, fHBP adsorption takes place at a pH which is equal to or below the aluminium hydroxyphosphate's point of zero charge (PZC), For a given aluminium hydroxyphosphate adjuvant, therefore, an aqueous medium (e.g. buffer) would be selected with a pH equal to or below the adjuvant's PZC. Conversely, for a given pH an aluminium hydroxyphosphate would be selected that has the same or a higher PZC. This selection of pH and PZC can give immunogenic compositions in which fHBP is stably adsorbed to an aluminium hydroxyphosphate.

In a second aspect, a fHBP and an aluminium hydroxyphosphate adjuvant are selected such that the fHBP has an isoelectric point (pI) within the range of 5.0 to 7.0 (inclusive) and the adjuvant's PZC is selected within the same range. By ensuring this close match of antigen and adjuvant characteristics it is possible to obtain stable adsorbed compositions even if the adsorption pH is above the adjuvant's PZC. Stable adsorption is facilitated by the presence of a buffer which can maintain pH also in the range of 5.0 to 7.0.

In a third aspect, if a fHBP has an isoelectric point above an aluminium hydroxyphosphate adjuvant's PZC then a buffer is added to bring the pH to within 1.2 pH units of the PZC.

Thus, for the first aspect, the invention provides a method for adsorbing a meningococcal fHBP antigen to an aluminium hydroxyphosphate adjuvant, wherein adsorption takes place at a pH which is equal to or below the aluminium hydroxyphosphate's point of zero charge. The adsorbed fHBP antigen can be used as an immunogen. The adsorption can be performed in various ways. Mixing of fHBP antigen, aluminium hydroxyphosphate and a buffer can occur in any suitable order, either by combining all three components separately or by pre-mixing two components and then mixing the pre-mix with the third component.

The invention also provides an immunogenic composition comprising a meningococcal fHBP antigen and an aluminium hydroxyphosphate adjuvant, wherein the aluminium hydroxyphosphate adjuvant has a point of zero charge which is higher than the immunogenic composition's pH.

For the second aspect, the invention provides a method for adsorbing a meningococcal fHBP antigen to an aluminium hydroxyphosphate adjuvant, wherein (i) the meningococcal fHBP antigen has an isoelectric point between 5.0 and 7.0, (ii) the aluminium hydroxyphosphate adjuvant has a point of zero charge between 5.0 and 7.0, and (iii) adsorption of the fHBP antigens takes place at a pH between 5.0 and 7.0.

The invention also provides an immunogenic composition comprising a meningococcal fHBP antigen adsorbed to an aluminium hydroxyphosphate adjuvant, wherein (i) the meningococcal fHBP antigen has an isoelectric point between 5.0 and 7.0, and (ii) the aluminium hydroxyphosphate adjuvant has a point of zero charge between 5.0 and 7.0. The composition typically includes a buffer to maintain pH in the range of 5.0 to 7.0.

For the third aspect, the invention provides a method for adsorbing a meningococcal fHBP antigen to an aluminium hydroxyphosphate adjuvant, wherein (i) the meningococcal fHBP antigen has an isoelectric point which is greater than the adjuvant's point of zero charge and (ii) adsorption takes place at a pH which is within 1.2 pH units of the adjuvant's point of zero charge. The pH during adsorption is preferably achieved by including a buffer which maintains the pH within 1.2 pH units of the adjuvant's point of zero charge.

The invention also provides an immunogenic composition comprising a meningococcal fHBP antigen adsorbed to an aluminium hydroxyphosphate adjuvant, wherein (i) the meningococcal fHBP antigen has an isoelectric point which is greater than the adjuvant's point of zero charge and (ii) the composition has a pH which is within 1.2 pH units of the adjuvant's point of zero charge. The composition may include a buffer which maintains the pH within 1.2 pH units of the adjuvant's PZC.

The invention is particularly useful in relation to compositions which include more than one variant of fHBP. As mentioned above, such compositions have previously been reported not to adsorb well to aluminium adjuvants with phosphate groups.

Thus the invention provides a method for adsorbing two different meningococcal fHBP antigens to an aluminium hydroxyphosphate adjuvant, wherein adsorption of both of the fHBP antigens takes place at a pH which is equal to or below the aluminium hydroxyphosphate's point of zero charge. The adsorbed fHBP antigens can be used for broad spectrum meningococcal immunisation. Mixing of fHBP antigens and aluminium hydroxyphosphate (and a buffer) can occur in any suitable order.

The invention also provides an immunogenic composition comprising two different meningococcal fHBP antigens, both of which are adsorbed to aluminium hydroxyphosphate adjuvant. The composition typically includes a buffer to control pH during and/or after adsorption.

The invention also provides an immunogenic composition comprising two different meningococcal fHBP antigens and an aluminium hydroxyphosphate adjuvant, wherein the aluminium hydroxyphosphate adjuvant has a point of zero charge which is higher than the immunogenic composition's pH.

The invention also provides a method for adsorbing two different meningococcal fHBP antigens to an aluminium hydroxyphosphate adjuvant, wherein (i) both of the meningococcal fHBP antigens have an isoelectric point between 5.0 and 7.0, (ii) the aluminium hydroxyphosphate adjuvant has a point of zero charge between 5.0 and 7.0, and (iii) adsorption of both of the fHBP antigens takes place at a pH between 5.0 and 7.0. Adsorption may take place in the presence of a buffer.

The invention also provides an immunogenic composition comprising two different meningococcal fHBP antigens, both of which are adsorbed to aluminium hydroxyphosphate adjuvant, wherein (i) both of the meningococcal fHBP antigens have an isoelectric point between 5.0 and 7.0, (ii) the aluminium hydroxyphosphate adjuvant has a point of zero charge between 5.0 and 7.0. The composition typically includes a buffer to maintain pH in the range of 5.0 to 7.0.

The invention also provides a method for adsorbing two different meningococcal fHBP antigens to an aluminium hydroxyphosphate adjuvant, wherein (i) the meningococcal fHBP antigens both have isoelectric points which are greater than the adjuvant's point of zero charge and (ii) adsorption of each antigen takes place at a pH which is within 1.2 pH units of the adjuvant's point of zero charge. The pH during adsorption is preferably achieved by including a buffer which maintains the pH within 1.2 pH units of the adjuvant's point of zero charge.

The invention also provides an immunogenic composition comprising two different meningococcal fHBP antigens, both adsorbed to aluminium hydroxyphosphate adjuvant, wherein (i) each meningococcal fHBP antigen has an isoelectric point which is greater than the adjuvant's point of zero charge and (ii) the composition has a pH which is within 1.2 pH units of the adjuvant's point of zero charge.

The invention also provides an immunogenic composition prepared by any of the above methods.

In compositions of the invention, the or each fHBP antigen is preferably at least 85% adsorbed, as described in more detail below.

Factor H Binding Protein(s)

Compositions of the invention include at least one meningococcal factor H binding protein (fHBP). Where a composition includes two different fHBPs these are preferably different variants as disclosed in reference 8. Different fHBPs will generate distinct immune responses which are not fully cross-reactive and which provide a broader spectrum of strain coverage against meningococci.

Where a composition comprises a single fHBP variant, it may include one of the following:
 (a) a first polypeptide comprising a first amino acid sequence, where the first amino acid sequence comprises an amino acid sequence (i) having at least a % sequence identity to SEQ ID NO: 1 and/or (ii) consisting of a fragment of at least x contiguous amino acids from SEQ ID NO: 1;
 (b) a second polypeptide, comprising a second amino acid sequence, where the second amino acid sequence comprises an amino acid sequence (i) having at least b % sequence identity to SEQ ID NO: 2 and/or (ii) consisting of a fragment of at least γ contiguous amino acids from SEQ ID NO: 2;
 (c) a third polypeptide, comprising a third amino acid sequence, where the third amino acid sequence comprises an amino acid sequence (i) having at least c % sequence identity to SEQ ID NO: 3 and/or (ii) consisting of a fragment of at least z contiguous amino acids from SEQ ID NO: 3.

Where a composition comprises two different meningococcal fHBP antigens, it may include a combination of: (i) a first and second polypeptide as defined above; (ii) a first and third polypeptide as defined above; or (iii) a second and third polypeptide as defined above. A combination of a first and third polypeptide is preferred. A combination in which each of the two different meningococcal fHBP antigens has a pI between 5.0 and 7.0 is preferred, and in particular when they both have a pI in the range of 5.0 to 6.0 or in the range 5.2 to 6.2.

Where a composition comprises two different meningococcal fHBP antigens, although these may share some sequences in common, the first, second and third polypeptides have different fHBP amino acid sequences.

A polypeptide comprising the first amino acid sequence will, when administered to a subject, elicit an antibody response comprising antibodies that bind to the wild-type meningococcus protein having nascent amino acid sequence SEQ ID NO: 20 (MC58). In some embodiments some or all of these antibodies do not bind to the wild-type meningococcus protein having nascent amino acid sequence SEQ ID NO: 21 or to the wild-type meningococcus protein having nascent amino acid sequence SEQ ID NO: 22.

A polypeptide comprising the second amino acid sequence will, when administered to a subject, elicit an antibody response comprising antibodies that bind to the wild-type meningococcus protein having nascent amino acid sequence SEQ ID NO: 21 (2996). In some embodiments some or all of these antibodies do not bind to the wild-type meningococcus protein having nascent amino acid sequence SEQ ID NO: 20 or to the wild-type meningococcus protein having nascent amino acid sequence SEQ ID NO: 22.

A polypeptide comprising the third amino acid sequence will, when administered to a subject, elicit an antibody response comprising antibodies that bind to the wild-type meningococcus protein having nascent amino acid sequence SEQ ID NO: 22 (M1239). In some embodiments some or all of these antibodies do not bind to the wild-type meningococcus protein having nascent amino acid sequence SEQ ID NO: 20 or to the wild-type meningococcus protein having nascent amino acid sequence SEQ ID NO: 21.

In some embodiments the fragment of at least x contiguous amino acids from SEQ ID NO: 1 is not also present within SEQ ID NO: 2 or within SEQ ID NO: 3. Similarly, the fragment of at least y contiguous amino acids from SEQ ID NO: 2 might not also be present within SEQ ID NO: 1 or within SEQ ID NO: 3. Similarly, the fragment of at least z contiguous amino acids from SEQ ID NO: 3 might not also be present within SEQ ID NO: 1 or within SEQ ID NO: 2. In some embodiments, when said fragment from one of SEQ ID NOs: 1 to 3 is aligned as a contiguous sequence against the other two SEQ ID NOs, the identity between the fragment and each of the other two SEQ ID NOs is less than 75% e.g. less than 70%, less than 65%, less than 60%, etc.

The value of a is at least 80 e.g. 82, 84, 86, 88, 90, 92, 94, 95, 96, 97, 98, 99 or more. The value of b is at least 80 e.g. 82, 84, 86, 88, 90, 92, 94, 95, 96, 97, 98, 99 or more. The value of c is at least 80 e.g. 82, 84, 86, 88, 90, 92, 94, 95, 96, 97, 98, 99 or more. The values of a, b and c may be the same or different. In some embodiments, a b and c are identical.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z may be the same or different. In some embodiments, x y and z are identical.

Fragments preferably comprise an epitope from the respective SEQ ID NO: sequence. Other useful fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of the respective SEQ ID NO: while retaining at least one epitope thereof.

Amino acid sequences used with the invention may, compared to SEQ ID NOs: 1, 2 or 3, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparaginie, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may have one or more (e.g. 1, 2, 3, 4, 5, 6, 7, 8, 9, 10, etc.) single amino acid deletions relative to a reference sequence. The polypeptides may also include one or more (e.g. 1, 2, 3, 4, 5, 6, 7, 8, 9, 10, etc.) insertions (e.g. each of 1, 2, 3, 4 or 5 amino acids) relative to a reference sequence.

A useful first amino acid sequence has at least 85% identity (e.g. >95% or 100%) to SEQ ID NO: 1. Another useful first amino acid sequence has at least 95% identity (e.g. >98% or 100%) to SEQ ID NO: 4. Another useful first amino acid sequence has at least 95% identity (e.g. >98% or 100%) to SEQ ID NO: 5.

A useful third amino acid sequence has at least 85% identity (e.g. >95% or 100%) to SEQ ID NO: 3. Another useful third amino acid sequence has at least 95% identity (e.g. >98% or 100%) to SEQ ID NO: 6.

Combinations comprising a mixture of first and third sequences based around SEQ ID NOs: 4 and 6 (or their close variants) are particularly useful. Another useful combination comprises a mixture of first and third sequences based around a mixture of SEQ ID NOs: 5 and 6 (or their close variants). Thus a composition may comprise a polypeptide comprising amino acid sequence SEQ ID NO: 23 and a polypeptide comprising amino acid sequence SEQ ID NO: 25.

Where a composition includes two meningococcal fHBP antigens, this may be in a bivalent fHBP composition, or there may be more than two different fHBP antigens e.g. in a trivalent or tetravalent fHBP composition.

In some embodiments fHBP polypeptide(s) are lipidated e.g. at a N-terminus cysteine. In other embodiments, however, fHBP polypeptide(s) are not lipidated. For lipidated fHBPs, lipids attached to cysteines will usually include palmitoyl residues e.g. as tripalmitoyl-S-glyceryl-cysteine (Pam3Cys), dipalmitoyl-S-glyceryl cysteine (Pam2Cys), N-acetyl (dipalmitoyl-S-giyceryl cysteine), etc. Examples of mature lipidated fHBP sequences are SEQ ID NO: 23 (including SEQ ID NO: 4), SEQ ID NO: 24 (including SEQ ID NO: 5), and SEQ ID NO: 25 (including SEQ ID NO: 6).

Administration of a fHBP will preferably elicit antibodies which can bind to a meningococcal polypeptide consisting of amino acid sequence SEQ ID NO: 1, 2 or 3. Advantageous fHBP antigens for use with the invention can elicit bactericidal anti-meningococcal antibodies after administration to a subject.

The total amount of a fHBP polypeptide will usually be between 1 and 500 μg/dose e.g. between 60 and 200 μg/dose or between 120 and 500 μg/ml. An amount of 20, 40, 50, 60, 80, 100 or 200 μg for each fHBP polypeptide is typical in a human vaccine dose. Thus a vaccine may be formulated to include this amount of each fHBP(s).

Where a composition comprises different meningococcal fHBP antigens, these may be present as separate polypeptides as described above (e.g. a first and second polypeptide) or they may be present as part of a single 'hybrid' polypeptide i.e. where at least two (e.g. 2, 3, 4, 5, or more) fHBP antigens are expressed as a single polypeptide chain, as disclosed for meningococcal antigens in reference 12.

A hybrid polypeptide may comprise two or three of the following: a first amino acid sequence as defined above; a second amino acid sequence as defined above; and/or a third amino acid sequence as defined above.

Hybrid polypeptides can be represented by the formula $NH_2$-A-{—X-L-}$_n$—B—COOH, wherein: X is a first, second or third amino acid sequence as defined above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3, and at least two of a first, second and third amino acid sequence are present.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {—X—L—}, linker amino acid sequence -L- may be present or absent. For instance, when n=2 the hybrid may be $NH_2$—$X_1$-$L_1$-$X_2$-$L_2$-COOH, $NH_2$—$X_1$-$L_1$-$X_2$—COOH, $NH_2$—$X_1$—$X_2$—$L_2$—COOH, etc. Linker amino acid sequence(s) —L— will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID NO: 15) or GSGSGGGG (SEQ ID NO: 16), with the Gly-Ser dipeptide being formed from a BamHI restriction site, thus aiding cloning and manipulation, and the (Gly)$_4$ tetrapeptide being a typical poly-glycine linker. Another suitable linker, particularly for use as the final $L_n$ is a Leu-Glu dipeptide.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more, such as SEQ ID NO: 17), or sequences which enhance protein stability. Other suitable C-terminal amino acid sequences will be apparent to those skilled in the art.

Aluminium Hydroxyphosphate Adjuvants and Adsorption

Compositions of the invention include an aluminium hydroxyphosphate adjuvant. Such adjuvants are often referred to for convenience as "aluminium phosphate" [13], although hydroxyphosphates can be distinguished from strict $AlPO_4$ by the presence of hydroxyl groups. For example, an IR spectrum band at 3164 cm$^{-1}$ (e.g. when heated to 200° C.) indicates the presence of structural hydroxyls. The aluminium hydroxyphosphate adjuvant may contain a small amount of sulfate (i.e. aluminium hydroxyphosphate sulfate) and may also include sodium and/or chloride ions [14]. The adjuvant may be obtained by precipitation.

Aluminium hydroxyphosphate is not a stoichiometric compound and its hydroxyl and phosphate composition depends on precipitation reactants and conditions. This hydroxyl/phosphate composition affects the adjuvant's point of zero charge (PZC; the pH at which a surface has zero net charge). The PZC is inversely related to the degree of substitution of phosphate for hydroxyl (the P/Al molar ratio). Substitution of phosphate anions for hydroxyl anions lowers the PZC. Thus the PZC can be altered by changing the concentration of free phosphate ions in solution (more phosphate=more acidic PZC) or by adding a buffer such as a histidine buffer (makes PZC more basic). Aluminium hydroxyphosphates used with the invention generally have a PZC of between 5.0 and 6.6 e.g. between 5.4 and 6.2.

The P/Al molar ratio of an aluminium hydroxyphosphate adjuvant will generally be between 0.3 and 1.2, preferably between 0.8 and 1.2, or between 0.85 and 1.0, and more preferably about 0.9. A P/Al molar ratio of at least 0.5 can provide an adjuvant with better aging properties.

The aluminium hydroxyphosphate will generally be amorphous (i.e. amorphous to X-rays). It will generally be particulate (e.g. plate-like morphology as seen in transmission electron micrographs). Typical diameters of the plates are 10-100 nm, and these form aggregates sized 0.5-2.0 μm (e.g. about 1-10 μm). Adsorptive capacities of between 0.7-1.5 mg protein per mg $Al^{+++}$ at pH 7.4 have been reported for aluminium hydroxyphosphate adjuvants.

A typical adjuvant is amorphous aluminium hydroxyphosphate with P/Al molar ratio between 0.84 and 0.92, and this adjuvant may be included at 0.6 mg $Al^{3+}$/ml.

The concentration of $Al^{+++}$ in a composition for administration to a patient is preferably less than 5 mg/ml e.g. ≤4 mg/ml, ≤3 mg/ml, ≤2 mg/ml, ≤1 mg/ml, etc. A preferred range is between 0.2 and 1 mg/ml. A maximum $Al^{+++}$ concentration of 0.85 mg/dose is preferred.

At least 85% (by weight) of a fHBP in a composition of the invention is adsorbed to aluminium hydroxyphosphate e.g. ≥90%, ≥95% or even 100%. The proportion of adsorbed fHBP can be controlled by altering salt concentration and/or pH during formulation e.g. in general, a higher NaCl concentration can decrease fHBP's adsorption. The amount of adsorption for any formulation will depend on a combination of parameters including the adjuvant's PZC, the salt concentration and pH during formulation, the adjuvant concentration, the antigen concentration and the antigen's pI. The impact of each of these parameters on adsorption can be readily assessed. The degree of adsorption can be determined by comparing the total amount of fHBP antigen in a composition (e.g. measured before adsorption occurs, or measured by desorbing adsorbed antigen) to the amount which remains in the supernatant after centrifugation (e.g. see chapter 4 of ref. 15). The absence of detectable antigen in the supernatant after centrifugation indicates that total adsorption has occurred i.e. all of the fHBP is in the pellet, which contains the insoluble adjuvant and its adsorbed content.

It is known to use mixtures of different aluminium salts in a single vaccine e.g. see reference 16. Although adjuvants including both aluminium hydroxyphosphate and hydroxide can be used with fHBP, it is preferred that a composition should not include any aluminium hydroxide adjuvant because, as described above, it can degrade certain antigens which may be admixed with the fHBP (in particular, conjugated bacterial capsular saccharides).

For the first aspect, the inventors have found that fHBP proteins can be efficiently adsorbed to an aluminium hydroxyphosphate adjuvant by ensuring that adsorption takes place at a pH which is equal to or below the adjuvant's PZC. Thus an adjuvant can be chosen with a PZC equal to or above a desired formulation pH, or else a pH can be chosen equal to or below a desired adjuvant's PZC. Adjuvant and antigen are combined under these conditions and adsorption is allowed to occur. The pH should not be so low as to prevent adsorption or to irreversibly denature the fHBP, Thus adsorption ideally occurs within 2 pH units (ideally within 1.2 pH units) of the PZC.

For the second aspect, the inventors have found that fHBP proteins can be efficiently adsorbed to an aluminium hydroxyphosphate adjuvant by using a meningococcal fHBP antigen with an isoelectric point between 5.0 and 7.0 and an aluminium hydroxyphosphate adjuvant with a point of zero charge also between 5.0 and 7.0. Adsorption takes place at a pH between 5.0 and 7.0, and pH may be maintained (before, during, and/or after adsorption) by including a buffer to maintain pH in the range of 5.0 to 7.0. Within the pH range of 5.0 and 7.0, a preferred sub-range is 5.0 to 6.0. The second aspect is not suitable for all fHBPs as some (e.g. SEQ ID NO: 20) have a pI outside the required range, but an appropriate fHBP can readily be selected.

The isoelectric point of a fHBP may be determined empirically by a technique such as isoelectric focusing. More conveniently, however, the isoelectric point is a theoretical isoelectric point. This may be calculated using pKa values of amino acids described in reference 17 e.g. using the relevant ExPASy tool [18]. For instance, nascent amino acid sequence SEQ ID NO: 20 has a predicted pI of 7.72 whereas SEQ ID NOs: 21 and 22 have predicted pIs of 5.87 and 6.15. Mature sequences SEQ ID NOs: 23, 24 and 25 (comprising SEQ ID NOs: 4, 5 and 6, respectively) all have a predicted pI in the relevant range: 5.46, 5.72 and 5.86, respectively. A correction for a blocked N-terminus amine (e.g. when lipidated) reduces the pI by about 0.1 but SEQ ID NOs: 23, 24 and 25 still have predicted pIs in the range from 5.0 to 6.0. Combinations where each different meningococcal fHBP antigen has a pI between 5.0 and 7.0 are preferred, and in particular when they both have a pI in the range of 5.0 to 6.0 or in the range 5.2 to 6.2.

A useful combination of fHBP antigens with pIs in the appropriate range may comprise a mixture of first and third sequences based around SEQ ID NOs: 4 and 6 (or their close variants) or a mixture of first and third sequences based around a mixture of SEQ ID NOs: 5 and 6 (or their close variants). Further details of such antigen pairings are provided above. For example, a combination of SEQ ID NOs: 23 and 25 is particularly useful, and these two proteins may be lipidated (as discussed above).

For the third aspect, the inventors have found that a meningococcal fHBP antigen with a pI greater than an aluminium hydroxyphosphate adjuvant's PZC can be efficiently adsorbed by ensuring that adsorption takes place at a pH within 1.2 pH units of the PZC. Adsorption may take place at a pH above or below the adjuvant's PZC, although the pH should not be so extreme as to irreversibly denature the fHBP. The pH during adsorption is preferably achieved by including a buffer which maintains the pH within 1.2 pH unite of the adjuvant's PZC. Where a pH is within 1.2 pH units, it may be within 1 pH unit or less e.g. within 0.8 pH unit, within 0.6 pH unit, within or 0.5 pH unit.

Order of Mixing

As mentioned above, the invention provides a method for adsorbing a meningococcal fHBP antigen to an aluminium hydroxyphosphate adjuvant. Mixing of fHBP antigen(s), aluminium hydroxyphosphate and any buffer can occur in any suitable order, either by combining all components separately or by pre-mixing two components and then mixing the pre-mix with the third component.

Thus, for example, in one embodiment the invention provides a process for preparing an immunogenic composition comprising a meningococcal fHBP antigen, comprising a step of combining a meningococcal fHBP antigen and an aluminium hydroxyphosphate adjuvant, wherein: (i) the aluminium hydroxyphosphate adjuvant has a point of zero charge; and (ii) the combining step occurs at a pH lower than the point of zero charge such that the fHBP antigen adsorbs to the adjuvant.

In another embodiment, the invention provides a process for preparing an immunogenic composition comprising a meningococcal fHBP antigen, comprising a step of combining a meningococcal fHBP antigen and an aluminium hydroxyphosphate adjuvant, wherein: (i) the aluminium hydroxyphosphate adjuvant has a point of zero charge; and (ii) the composition has a pH lower than the point of zero charge, such that the fHBP antigen adsorbs to the adjuvant.

In another embodiment, the invention provides a process for preparing an immunogenic composition comprising a meningococcal fHBP antigen, comprising steps of: (i) providing an aqueous composition comprising a meningococcal fHBP antigen and having a pH; (ii) providing an aluminium hydroxyphosphate adjuvant having a point of zero charge which is higher than said pH; and (iii) combining the aqueous composition with the aluminium hydroxyphosphate adjuvant to give the immunogenic composition.

In another embodiment, the invention provides a process for preparing an immunogenic composition comprising a meningococcal fHBP antigen, comprising steps of: (i) providing an aqueous composition comprising an aluminium hydroxyphosphate adjuvant and having a pH, wherein the aluminium hydroxyphosphate adjuvant has a point of zero charge which is higher than said pH; and (ii) combining the aqueous composition with a meningococcal fHBP antigen to give the immunogenic composition.

In another embodiment, the invention provides a process for preparing an immunogenic composition comprising a meningococcal fHBP antigen, comprising steps of: (i) providing a first aqueous composition having a pH; (ii) providing a second aqueous composition comprising a meningococcal fHBP antigen and an aluminium hydroxyphosphate adjuvant having a point of zero charge which is higher than said pH; and (iii) combining the first and second aqueous compositions to give the immunogenic composition.

In another embodiment, the invention provides a process for preparing an immunogenic composition comprising a meningococcal fHBP antigen, comprising steps of: (i) providing a first aqueous composition having a pH; (ii) providing a second aqueous composition comprising a meningococcal fHBP antigen; and (iii) providing an aluminium hydroxyphosphate adjuvant having a point of zero charge which is higher than said pH; and (iv) combining in any order the first aqueous composition, the second aqueous composition and the aluminium hydroxyphosphate, to give the immunogenic composition.

The invention also provides a method for adsorbing two different meningococcal fHBP antigens to an aluminium hydroxyphosphate adjuvant, wherein adsorption of both of the fHBP antigens takes place at a pH which is equal to or below the aluminium hydroxyphosphate's point of zero charge. Again, mixing of fHBP antigens, aluminium hydroxyphosphate and a buffer can occur in any suitable order.

Thus, in one embodiment, the two different fHBP antigens are separately adsorbed to aluminium hydroxyphosphate at the appropriate pH, and the two adsorbed antigens can then be mixed.

In another embodiment, the two different fHBP antigens are mixed with each other and the mixture is then added to aluminium hydroxyphosphate, where the aluminium hydroxyphosphate is either at an appropriate pH for adsorption or where the pH is adjusted after addition of the mixture.

In another embodiment, the two different fHBP antigens are added sequentially to aluminium hydroxyphosphate, where the aluminium hydroxyphosphate is either at an appropriate pH for adsorption or where the pH is adjusted after addition of one or both fHBP antigens.

In another embodiment, one fHBP antigen is mixed with aluminium hydroxyphosphate and then the other fHBP antigen is added to the mixture, where the aluminium hydroxyphosphate is either at an appropriate pH for adsorption before addition of the first fHBP antigen, or where the pH is adjusted after addition of the first fHBP antigen, or where the pH is adjusted before addition of the second fHBP antigen, or where the pH is adjusted after addition of the second fHBP antigen.

These and other possibilities are available to the skilled person for all embodiments of the invention.

An Alternative Adjuvant

As an alternative to using an aluminium hydroxyphosphate adjuvant, the invention can use a particulate complex of an immunostimulatory oligonucleotide and a polycationic polymer, such as "IC31". Definitions given above can be amended accordingly. For instance, the invention provides an immunogenic composition comprising a meningococcal fHBP antigen and a particulate complex of an immunostimulatory oligonucleotide and a polycationic polymer. The invention also provides an immunogenic composition comprising two different meningococcal fHBP antigens and a particulate complex of an immunostimulatory oligonucleotide and a polycationic polymer.

Immunostimulatory oligonucleotides are known as useful adjuvants. They often contain a CpG motif (a dinucleotide sequence containing an unmethylated cytosine linked to a guanosine) and their adjuvant effect is discussed in refs. 19-24. Oligonucleotides containing TpG motifs, palindromic sequences, multiple consecutive thymidine nucleotides (e.g. TTTT), multiple consecutive cytosine nucleotides (e.g. CCCC) or poly(dG) sequences are also known immunostimulants, as are double-stranded RNAs. Although any of these various immunostimulatory oligonucleotides can be used with the invention, it is preferred to use an oligodeoxynucleotide containing deoxyinosine and/or deoxyuridine, and ideally an oligodeoxynucleotide containing deoxyinosine and deoxycytosine. Inosine-containing oligodeoxynucleotides may include a CpI motif (a dinucleotide sequence containing a cytosine linked to an inosine). The oligodeoxynucleotide may include more than one (e.g. 2, 3, 4, 5, 6 or more) CpI motif, and these may be directly repeated (e.g. comprising the sequence $(CI)_x$, where x is 2, 3, 4, 5, 6 or more) or separated from each other (e.g. comprising the sequence $(CIN)_x$, where x is 2, 3, 4, 5, 6 or more, and where each N independently represents one or more nucleotides). Cytosine residues are ideally unmethylated.

An oligonucleotide will typically have between 10 and 100 nucleotides e.g. 15-50 nucleotides, 20-30 nucleotides, or 25-28 nucleotides. It will typically be single-stranded.

The oligonucleotide can include exclusively natural nucleotides, exclusively non-natural nucleotides, or a mix of both. For instance, it may include one or more phosphorothioate linkage(s), and/or one or more nucleotides may have a 2'-O-methyl modification.

A preferred oligonucleotide is a single-stranded deoxynucleotide comprising the 26-mer sequence 5'-$(IC)_{13}$-3' (SEQ ID NO: 18). This oligodeoxynucleotide forms stable complexes with polycationic polymers to give a good adjuvant.

The polycationic polymer is ideally a polycationic peptide. The polymer may include one or more leucine amino acid residue(s) and/or one or more lysine amino acid residue(s). The polymer may include one or more arginine amino acid residue(s). It may include at least one direct repeat of one of these amino acids e.g. one or more Leu-Leu dipeptide sequence(s), one or more Lys-Lys dipeptide sequence(s), or one or more Arg-Arg dipeptide sequence(s). It may include at least one (and preferably multiple e.g. 2 or 3) Lys-Leu dipeptide sequence(s) and/or at least one (and preferably multiple e.g. 2 or 3) Lys-Leu-Lys tripeptide sequence(s).

The peptide may comprise a sequence $R_1$—$XZXZ_xXZX$—$R_2$, wherein: x is 3, 4, 5, 6 or 7; each X is independently a positively-charged natural and/or non-natural amino acid residue; each Z is independently an amino acid residue L, V, I, F or W; and $R_1$ and $R_2$ are independently selected from the group consisting of —H, —$NH_2$, —$COCH_3$, or —COH. In some embodiments X—$R_2$ may be an amide, ester or thioester of the peptide's C-terminal amino acid residue.

A polycationic peptide will typically have between 5 and 50 amino acids e.g. 6-20 amino acids, 7-15 amino acids, or 9-12 amino acids.

A peptide can include exclusively natural amino acids, exclusively non-natural amino acids, or a mix of both. It may include L-amino acids and/or D-amino acids. L-amino acids are typical.

A peptide can have a natural N-terminus ($NH_2$—) or a modified N-terminus e.g. a hydroxyl, acetyl, etc. A peptide can have a natural C-terminus (—COOH) or a modified C-terminus e.g. a hydroxyl, an acetyl, etc. Such modifications can improve the peptide's stability.

A preferred peptide for use with the invention is the 11-mer KLKLLLLLKLK (SEQ ID NO: 19), with all L-amino acids. The N-terminus may be deaminated and the C-terminus may be hydroxylated. A preferred peptide is H—KLKL$_5$KLK—OH, with all L-amino acids. This oligopeptide forms stable complexes with immunostimulatory oligonucleotides to give a good adjuvant.

The most preferred mixture of immunostimulatory oligonucleotide and polycationic polymer is the TLR9 agonist known as IC31™ [25-27], which is an adsorptive complex of oligodeoxynucleotide SEQ ID NO: 18 and polycationic oligopeptide SEQ ID NO: 19.

The oligonucleotide and oligopeptide can be mixed together at various ratios, but they will generally be mixed with the peptide at a molar excess. The molar excess may be at least 5:1 e.g. 10:1, 15:1, 20:1, 25:1, 30:1, 35:1, 40:1 etc. A molar ratio of about 25:1 is ideal [28,29]. Mixing at this excess ratio can result in formation of insoluble particulate complexes between oligonucleotide and oligopeptide. The complexes can be combined with an oil-in-water emulsion.

The oligonucleotide and oligopeptide will typically be mixed under aqueous conditions e.g. a solution of the oligonucleotide can be mixed with a solution of the oligopeptide with a desired ratio. The two solutions may be prepared by dissolving dried (e.g. lyophilised) materials in water or buffer to form stock solutions that can then be mixed. The complexes can be analysed using the methods disclosed in reference 30.

Poly-arginine and CpG oligodeoxynucleotides similarly form complexes [31] which may be used.

The complexes can be maintained in aqueous suspension e.g. in water or in buffer. Typical buffers for use with the complexes are phosphate buffers (e.g. phosphate-buffered saline), Tris buffers, Tris/sorbitol buffers, borate buffers, succinate buffers, citrate buffers, histidine buffers, etc. As an alternative, complexes may sometimes be lyophilised.

Various concentrations of oligonucleotide and polycationic polymer can be used e.g. any of the concentrations used in references 25, 28 or 29. For example, a polycationic oligopeptide can be present at 1100 µM, 1000 µM, 350 µM, 220 µM, 200 µM, 110 µM, 100 µM, 11 µM, 10 µM, etc. An oligonucleotide can be present at 44 nM, 40 nM, 14 nM, 4.4 nM, 4 nM, etc. A polycationic oligopeptide concentration of less than 2000 nM is typical. For SEQ ID NOs: 18 & 19, mixed at a molar ratio of 1:25, the concentrations in mg/mL in three embodiments of the invention may thus be 0.311 & 1.322, or 0.109 & 0.463, or 0.031 and 0.132.

In embodiments of the invention which include a particulate complex of an immunostimulatory oligonucleotide and a polycationic polymer, it is useful if this complex is the sole adjuvant e.g. the composition may be free from aluminium salts and free from oil-in-water emulsions.

In a specific embodiment, the invention provides an immunogenic composition comprising: a particulate complex of an immunostimulatory oligonucleotide and a polycationic polymer (e.g. IC31); a meningococcal fHBP antigen; and conjugated capsular saccharides from 1, 2, 3 or 4 of meningococcal serogroups A, C, W135 and/or Y. Further details of suitable conjugated saccharides are given below.

Further Antigen(s)

In addition to fHBP antigen(s), compositions of the invention can include further antigens from meningococcus or from other pathogens e.g. from other bacteria such as pneumococcus.

Further Meningococcal Polypeptide Antigens

In addition to including meningococcal fHBP polypeptide antigen(s), a composition may include one or more further meningococcal polypeptide antigen(s). Thus a composition may include a polypeptide antigen selected from the group consisting of: 287, NadA, NspA, HmbR, NhhA, App, and/or Omp85. These antigens will usefully be present as purified polypeptides e.g. recombinant polypeptides. The antigen will preferably elicit bactericidal anti-meningococcal antibodies after administration to a subject. If a composition includes a PorA antigen then, in some embodiments, only one meningococcal PorA serosubtype is included. In some embodiments, no meningococcal PorA outer membrane protein is included in a composition.

A composition of the invention may include a 287 antigen. The 287 antigen was included in the published genome sequence for meningococcal serogroup B strain MC58 [32] as gene NMB2132 (GenBank accession number GI:7227388; SEQ ID NO: 9 herein). The sequences of 287 antigen from many strains have been published since then. For example, allelic forms of 287 can be seen in FIGS. 5 and 15 of reference 33, and in example 13 and FIG. 21 of reference 34 (SEQ IDs 3179 to 3184 therein). Various immunogenic fragments of the 287 antigen have also been reported. Preferred 287 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) comprising a fragment of at least 'n' consecutive amino acids of SEQ ID NO: 9, wherein V is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 9. The most useful 287 antigens of the invention can elicit antibodies which, after administration to a subject, can bind to a meningococcal polypeptide consisting of amino acid sequence SEQ ID NO: 9. Advantageous 287 antigens for use with the invention can elicit bactericidal anti-meningococcal antibodies after administration to a subject.

A composition of the invention may include a NadA antigen. The NadA antigen was included in the published genome sequence for meningococcal serogroup B strain MC58 [32] as gene NMB1994 (GenBank accession number GI:7227256; SEQ ID NO: 10 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least W consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10. The most useful NadA antigens of the invention can elicit antibodies which, after administration to a subject, can bind to a meningococcal polypeptide consisting of amino acid sequence SEQ ID NO: 10. Advantageous NadA antigens for use with the invention can elicit bactericidal anti-meningococcal antibodies after administration to a subject. SEQ ID NO: 6 is one such fragment.

A composition of the invention may include a NspA antigen. The NspA antigen was included in the published genome sequence for meningococcal serogroup B strain MC58 [32] as gene NMB0663 (GenBank accession number GI:7225888; SEQ ID NO: 11 herein). The antigen was previously known from references 35 & 36. The sequences of NspA antigen from many strains have been published since then. Various immunogenic fragments of NspA have also been reported. Preferred NspA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11. The most useful NspA antigens of the invention can elicit antibodies which, after administration to a subject, can bind to a meningococcal polypeptide consisting of amino acid sequence SEQ ID NO: 11. Advantageous NspA antigens for use with the invention can elicit bactericidal anti-meningococcal antibodies after administration to a subject.

Compositions of the invention may include a meningococcal HmbR antigen. The full-length HmbR sequence was included in the published genome sequence for meningococcal serogroup B strain MC58 [32] as gene NMB1668 (SEQ ID NO: 7 herein). Reference 37 reports a HmbR sequence from a different strain (SEQ ID NO: 8 herein). SEQ ID NOs: 7 and 8 differ in length by 1 amino acid and have 94.2% identity. The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 7, where the value of i is 50, 60, 70, 80, 90, 95, 99 or more. In other embodiments a HmbR sequence used according to the invention may comprise a fragment of at least j consecutive amino acids from SEQ ID NO: 7, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 7 and/or (ii) comprising a fragment of at least j consecutive amino acids from SEQ ID NO: 7. Preferred fragments of j amino acids comprise an epitope from SEQ ID NO: 7, Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional, residues, were investigated in reference 38. The most useful HmbR antigens of the invention can elicit antibodies which, after administration to a subject, can bind to a meningococcal polypeptide consisting of amino acid sequence SEQ ID NO: 7. Advantageous HmbR antigens for use with the invention can elicit bactericidal anti-meningococcal antibodies after administration to a subject.

A composition of the invention may include a NhhA antigen. The NhhA antigen was included in the published genome sequence for meningococcal serogroup B strain MC58 [32] as gene NMB0992 (GenBank accession number GI:7226232; SEQ ID NO: 12 herein). The sequences of NhhA antigen from many strains have been published since e.g. refs 33 & 39, and various immunogenic fragments of NhhA have been reported. It is also known as Hsf. Preferred NhhA antigens for use with the invention comprise an amino acid sequence: (a) having 50% or more identity (e.g. 60%. 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12. The most useful NhhA antigens of the invention can elicit antibodies which, after administration to a subject, can bind to a meningococcal polypeptide consisting of amino acid sequence SEQ ID NO: 12. Advantageous NhhA antigens for use with the invention can elicit bactericidal anti-meningococcal antibodies after administration to a subject.

A composition of the invention may include an App antigen. The App antigen was included in the published genome sequence for meningococcal serogroup B strain MC58 [32] as gene NMB1985 (GenBank accession number GI:7227246; SEQ ID NO: 13 herein). The sequences of App antigen from many strains have been published since then. Various immunogenic fragments of App have also been reported. Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least W consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13. The most useful App antigens of the invention can elicit antibodies which, after administration to a subject, can bind to a meningococcal polypeptide consisting of amino acid sequence SEQ ID NO: 13. Advantageous App antigens for use with the invention can elicit bactericidal anti-meningococcal antibodies after administration to a subject.

A composition of the invention may include an Omp85 antigen. The Omp85 antigen was included in the published genome sequence for meningococcal serogroup B strain MC58 [32] as gene NMB0182 (GenBank accession number GI:7225401; SEQ ID NO: 14 herein). The sequences of Omp85 antigen from many strains have been published since then. Further information on Omp85 can be found in references 40 and 41. Various immunogenic fragments of Omp85 have also been reported. Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 14. The most useful Omp85 antigens of the invention can elicit antibodies which, after administration to a subject, can bind to a meningococcal polypeptide consisting of amino acid sequence SEQ ID NO: 14. Advantageous Omp85 antigens for use with the invention can elicit bactericidal anti-meningococcal antibodies after administration to a subject.

Meningococcal Lipooligosaccharide

In addition to including meningococcal fHBP polypeptide antigen(s), a composition may include one or more meningococcal lipooligosaccharide (LOS) antigen(s). Meningococcal LOS is a glucosamine-based phospholipid that is found in the outer monolayer of the outer membrane of the bacterium. It includes a lipid A portion and a core oligosaccharide region, with the lipid A portion acting as a hydrophobic anchor in the membrane. Heterogeneity within the oligosaccharide core generates structural and antigenic diversity among different meningococcal strains, which has been used to subdivide the strains into 12 immunotypes (L1 to L12). The invention may use LOS from any immunotype e.g. from L1, L2, L3, L4, L5, L6, L7 and/or L8.

The L2 and L3 α-chains naturally include lacto-N-neotetraose (LNnT). Where the invention uses LOS from a L2 or L3 immunotype this LNnT may be absent. This absence can be achieved conveniently by using mutant strains that are engineered to disrupt their ability to synthesise the LNnT tetrasaccharide within the α-chain. It is known to achieve this goal by knockout of the enzymes that are responsible for the relevant biosynthetic additions [42,43]. For instance, knockout of the LgtB enzyme prevents addition of the terminal galactose of LNnT, as well as preventing downstream addition of the α-chain's terminal sialic acid. Knockout of the LgtA enzyme prevents addition of the N-acetylglucosamine of LNnT, and also the downstream additions. LgtA knockout may be accompanied by LgtC knockout. Similarly, knockout of the LgtE and/or GalE enzyme prevents addition of internal galactose, and knockout of LgtF prevents addition of glucose to the $Hep^1$ residue. Any of these knockouts can be used, singly or in combination, to disrupt the LNnT tetrasaccharide in a L2, L3, L4, L7 or L9 immunotype strain. Knockout of at least LgtB is preferred, as this provides a LOS that retains useful immunogenicity while removing the LNnT epitope.

In addition to, or in place of, mutations to disrupt the LNnT epitope, a knockout of the galE gene also provides a useful modified LOS, and a lipid A fatty transferase gene may similarly be knocked out [44]. At least one primary O-linked fatty acid may be removed from LOS [45]. LOS having a reduced number of secondary acyl chains per LOS molecule can also be used [46]. The LOS will typically include at least the GlcNAc-$Hep_2$phosphoethanolamine-$KDO_2$-Lipid A structure [47]. The LOS may include a GlcNAcβ1-3Galβ14Glc trisaccharide while lacking the LNnT tetrasaccharide.

LOS may be included in compositions of the invention in various forms. It may be used in purified form on its own. It may be conjugated to a carrier protein. When LOS is conjugated, conjugation may be via a lipid A portion in the LOS or by any other suitable moiety e.g. its KDO residues. If the lipid A moiety of LOS is absent then such alternative linking is required. Conjugation techniques for LOS are known from e.g. references 45, 47, 48, 49, etc. Useful carrier proteins for these conjugates are discussed below e.g. bacterial toxins, such as diphtheria or tetanus toxins, or toxoids or mutants thereof.

The LOS may be from a strain (e.g. a genetically-engineered meningococcal strain) which has a fixed (i.e. not phase variable) LOS immunotype as described in reference 50. For example, L2 and L3 LOS immunotypes may be fixed. Such strains may have a rate of switching between immunotypes that is reduced by more than 2-fold (even >50_fold) relative to the original wild-type strain. Reference 50 discloses how this result can be achieved by modification of the IgtA and/or IgtG gene products.

LOS may be O-acetylated on a GlcNac residue attached to its Heptose II residue e.g. for L3 [51].

An immunogenic composition can include more than one type of LOS e.g. LOS from meningococcal immunotypes L2 and L3. For example, the LOS combinations disclosed in reference 52 may be used.

A LOS antigen can preferably elicit bactericidal anti-meningococcal antibodies after administration to a subject.

However, preferred compositions of the invention are free from meningococcal lipooligosaccharide.

Meningococcal Capsular Saccharide Antigen(s)

In addition to including meningococcal fHBP polypeptide antigen(s), a composition may include one or more meningococcal capsular saccharide conjugates. A composition of the invention may include one or more conjugates of capsular saccharides from 1, 2, 3, or 4 of meningococcal serogroups A, C, W135 and Y e.g. A+C, A+W135, A+Y, C+W135, C+Y, W135+Y, A+C+W135, A+C+Y, A+W135+Y, A+C+W135+Y, etc. Compositions including a conjugated serogroup C capsular saccharide are useful, and compositions including saccharides from all four of serogroups A, C, W135 and Y are ideal.

The capsular saccharide of serogroup A meningococcus is a homopolymer of (α1→6)-linked N-acetyl-D-mannosamine-1-phosphate, with partial O-acetylation in the C3 and C4 positions. Acetylation at the C-3 position can be 70-95%. Conditions used to purify the saccharide can result in de-O-acetylation (e.g. under basic conditions), but it is useful to retain OAc at this C-3 position. In some embodiments, at least 50% (e.g. at least 60%, 70%, 80%, 90%, 95% or more) of the mannosamine residues in a serogroup A saccharides are O-acetylated at the C-3 position. Acetyl groups can be replaced with blocking groups to prevent hydrolysis [53], and such modified saccharides are still serogroup A saccharides within the meaning of the invention.

The serogroup C capsular saccharide is a homopolymer of (α2→9)-linked sialic acid (N-acetyl neuraminic acid, or 'NeuNAc'). The saccharide structure is written as →9)-Neu p NAc 7/8 OAc-(α2→. Most serogroup C strains have O-acetyl groups at C-7 and/or C-8 of the sialic acid residues, but about 15% of clinical isolates lack these O-acetyl groups [54,55]. The presence or absence of OAc groups generates unique epitopes, and the specificity of antibody binding to the saccharide may affect its bactericidal activity against O-acetylated (OAc+) and de-O-acetylated (OAc−) strains [56-58]. Serogroup C saccharides used with the invention may be prepared from either OAc+ or OAc− strains. Licensed MenC conjugate vaccines include both OAc− (NEISVAC-C™) and OAc+ (MENJUGATE™ & MENINGITEC™) saccharides. In some embodiments, strains for production of serogroup C conjugates are OAc+ strains, e.g. of serotype 16, serosubtype P1.7a,1, etc. Thus C:16:P1.7a,1 OAc+ strains may be used. OAc+ strains in serosubtype P1.1 are also useful, such as the C11 strain.

The serogroup W135 saccharide is a polymer of sialic acid-galactose disaccharide units. Like the serogroup C saccharide, it has variable O-acetylation, but at sialic acid 7 and 9 positions [59]. The structure is written as: →4)-D-Neup5Ac(7/9OAc)-α-(2→6)-D-Gal-α-(1→.

The serogroup Y saccharide is similar to the serogroup W135 saccharide, except that the disaccharide repeating unit includes glucose instead of galactose. Like serogroup W135, it has variable O-acetylation at sialic acid 7 and 9 positions [59]. The serogroup Y structure is written as: →4)-D-Neup5Ac(7/9OAc)-α-(2→6)-D-Glc-α-(1→.

The saccharides used according to the invention may be O-acetylated as described above (e.g. with the same O-acetylation pattern as seen in native capsular saccharides), or they may be partially or totally de-O-acetylated at one or more positions of the saccharide rings, or they may be hyper-O-acetylated relative to the native capsular saccharides.

The saccharide moieties in conjugates may comprise full-length saccharides as prepared from meningococci, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. One depolymerisation method involves the use of hydrogen peroxide. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis. Other depolymerisation methods are known in the art. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides, in some embodiments, saccharides have the following range of average degrees of polymerisation (Dp): A=10-20; C=12-22; W135=15-25. In terms of molecular weight, rather than Dp, useful ranges are, for all serogroups: <100 kDa; 5 kDa-75 kDa; 7 kDa-50 kDa; 8 kDa-35 kDa; 12 kDa-25 kDa; 15 kDa-22 kDa.

In some embodiments, the average molecular weight for saccharides from each of meningococcal serogroups A, C, W135 and Y may be more than 50 kDa e.g. ≥75 kDa, ≥100 kDa, ≥110 kDa, ≥120 kDa, ≥130 kDa, etc. [60], and even up to 1500 kDa, in particular as determined by MALLS. For instance: a Men A saccharide may be in the range 50-500 kDa e.g.60-80 kDa; a MenC saccharide may be in the range 100-210 kDa; a MenW135 saccharide may be in the range 60-190 kDa e.g. 120-140 kDa; and/or a MenY saccharide may be in the range 60-190 kDa e.g. 150-160 kDa.

The mass of meningococcal saccharide per serogroup in a composition will usually be between 1 μg and 20 μg e.g. between 2 and 10 μg per serogroup, or about 4 μg or about 5 μg or about 10 μg. Where conjugates from more than one serogroup are included then they may be present at substantially equal masses e.g. the mass of each serogroup's saccharide is within +10% of each other. As an alternative to an equal ratio, a double mass of serogroup A saccharide may be used. Thus a vaccine may include MenA saccharide at 10 μg and MenC, W135 and Y saccharides at 5 μg each.

Useful carrier proteins for meningococcal conjugates include bacterial toxins, such as diphtheria or tetanus toxins, or toxoids or mutants thereof. These are commonly used in conjugate vaccines. For example, the CRM197 diphtheria toxin mutant is useful [61]. Other suitable carrier proteins include synthetic peptides [62,63], heat shock proteins [64, 65], pertussis proteins [66,67], cytokines [68], lymphokines [68], hormones [68], growth factors [68], artificial proteins comprising multiple human $CD^+$ T cell epitopes from various pathogen-derived antigens [69] such as N19 [70], protein D from *H. influenzae* [71-73], pneumolysin [74] or its non-toxic derivatives [75], pneumococcal surface protein PspA [76], iron-uptake proteins [77], toxin A or B from *C. difficile* [78], recombinant *Pseudomonas aeruginosa* exoprotein A (rEPA) [79], etc. CRM197 is preferred.

Where a composition includes conjugates from more than one meningococcal serogroup it is possible to use the same carrier protein for each separate conjugate, or to use different carrier proteins. In both cases, though, a mixture of different conjugates will usually be formed by preparing each serotype conjugate separately, and then mixing them to form a mixture of separate conjugates.

Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. As described in reference 80, different meningococcal serogroup conjugates in a mixture can have different saccharide:protein ratios e.g. one may have a ratio of between 1:2 & 1:5, whereas another has a ratio between 5:1 & 1:1.99.

A carrier protein may be covalently conjugated to a meningococcal saccharide directly or via a linker. Various linkers are known. For example, attachment may be via a carbonyl, which may be formed by reaction of a free hydroxyl group of a modified saccharide with GDI [81,82] followed by reaction with a protein to form a carbamate linkage. Carbodiimide condensation can be used [83]. An adipic acid linker can be used, which may be formed by coupling a free —$NH_2$ group (e.g. introduced to a saccharide by amination) with adipic acid (using, for example, diimide activation), and then coupling a protein to the resulting saccharide-adipic acid intermediate [84,85]. Other linkers include β-propionamido [86], nitrophenyl-ethylamine [87], haloacyl halides [88], glycoside linkages [89], 6-aminocaproic acid [90], N-succinimidyl-3-(2-pyridyldithio)-propionate (SPDP) [91], adipic acid dihydrazide ADH [92], $C_4$ to $C_{12}$ moieties [93], etc.

Conjugation via reductive amination can be used. The saccharide may first be oxidised with periodate to introduce an aldehyde group, which can then form a direct covalent linkage to a carrier protein via reductive animation e.g. to the ε-amino group of a lysine. If the saccharide includes multiple aldehyde groups per molecule then this linkage technique can lead to a cross-linked product, where multiple aldehydes react with multiple carrier amines.

As described in reference 94, a mixture can include one conjugate with direct saccharide/protein linkage and another conjugate with linkage via a linker. This arrangement applies particularly when using saccharide conjugates from different meningococcal serogroups e.g. MenA and MenC saccharides may be conjugated via a linker, whereas MenW135 and MenY saccharides may be conjugated directly to a carrier protein.

A meningococcal saccharide may comprise a full-length intact saccharide as prepared from meningococcus, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. Depolymerisation can be used in order to provide an optimum chain length for immunogenicity and/or to reduce chain length for physical manageability of the saccharides.

Conjugated Pneumococcal Capsular Saccharide(s)

Compositions of the invention may include a pneumococcal capsular saccharide conjugated to a carrier protein.

The invention can include capsular saccharide from one or more different pneumococcal serotypes. Where a composition includes saccharide antigens from more than one serotype, these are preferably prepared separately, conjugated separately, and then combined. Methods for purifying pneumococcal capsular saccharides are known in the art (e.g. see reference 95) and vaccines based on purified saccharides from 23 different serotypes have been known for many years. Improvements to these methods have also been described e.g. for serotype 3 as described in reference 96, or for serotypes 1, 4, 5, 6A, 6B, 7F and 19A as described in reference 97.

Pneumococcal capsular saccharide(s) will typically be selected from the following serotypes: 1, 2, 3, 4, 5, 6A, 6B, 7F, 8, 9N, 9V, 10A, 11A, 12F, 14, 15B, 17F, 18C, 19A, 19F, 20, 22F, 23F and/or 33F. Thus, in total, a composition may include a capsular saccharide from 1, 2, 3, 4, 5, 6, 7, 8, 9, 10, 11, 12, 13, 14, 15, 16, 17, 18, 19, 20, 21, 22, 23 or more different serotypes.

A useful combination of serotypes is a 7-valent combination e.g. including capsular saccharide from each of serotypes 4, 6B, 9V, 14, 18C, 19F, and 23F. Another useful combination is a 9-valent combination e.g. including capsular saccharide from each of serotypes 1, 4, 5, 6B, 9V, 14, 18C, 19F and 23F. Another useful combination is a 10-valent combination e.g. including capsular saccharide from each of serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; or 22F and 15B. A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F; 6A and 19A, etc.

Thus a useful 13-valent combination includes capsular saccharide from serotypes 1, 3, 4, 5, 6A, 6B, 7F, 9V, 14, 18C, 19, 19F and 23 F e.g. prepared as disclosed in references 98 to 101. One such combination includes serotype 6B saccharide at about 8 µg/ml and the other 12 saccharides at concentrations of about 4 µg/ml each. Another such combination includes serotype 6A and 6B saccharides at about 8 µg/ml each and the other 11 saccharides at about 4 µg/ml each.

Suitable carrier proteins for conjugates are discussed above in relation to meningococcal conjugates. Particularly useful carrier proteins for pneumococcal conjugate vaccines are CRM197, tetanus toxoid, diphtheria toxoid and *H. influenzae* protein D. CRM197 is used in PREVNAR™, A 13-valent mixture may use CRM197 as the carrier protein for each of the 13 conjugates, and CRM197 may be present at about 55-60 µg/ml.

Where a composition includes conjugates from more than one pneumococcal serotype, it is possible to use the same carrier protein for each separate conjugate, or to use different carrier proteins. In both cases, though, a mixture of different conjugates will usually be formed by preparing each serotype conjugate separately, and then mixing them to form a mixture of separate conjugates. Reference 102 describes potential advantages when using different carrier proteins in multivalent pneumococcal conjugate vaccines, but the PREVNAR™ product successfully uses the same carrier for each of seven different serotypes.

A carrier protein may be covalently conjugated to a pneumococcal saccharide directly or via a linker, as discussed above in relation to meningococcal conjugates. Cross-linking conjugation techniques are particularly useful for at least pneumococcal serotypes 4, 6B, 9V, 14, 18C, 19F and 23F.

As discussed above for meningococcal saccharides, a pneumococcal saccharide may comprise a full-length intact saccharide as prepared from pneumococcus, and/or may comprise fragments of full-length saccharides. Where more than one pneumococcal serotype is used then it is possible to use intact saccharides for each serotype, fragments for each serotype, or to use intact saccharides for some serotypes and fragments for other serotypes. Where a composition includes saccharide from any of serotypes 4, 6B, 9V, 14, 19F and 23F, these saccharides are preferably intact. In contrast, where a composition includes serotype 18C saccharide it is preferably depolymerised.

A serotype 3 saccharide may also be depolymerised. For instance, a serotype 3 saccharide can be subjected to acid hydrolysis for depolymerisation [98] e.g. using acetic acid. The resulting fragments may then be oxidised for activation (e.g. periodate oxidation, maybe in the presence of bivalent cations e.g. with $MgCl_2$), conjugated to a carrier (e.g. CRM197) under reducing conditions (e.g. using sodium cyanoborohydride), and then (optionally) any unreacted aldehydes in the saccharide can be capped (e.g. using sodium borohydride) [98], Conjugation may be performed on lyophilized material e.g. after co-lyophilizing activated saccharide and carrier.

A serotype 1 saccharide may be at least partially de-O-acetylated e.g. achieved by alkaline pH buffer treatment [99] such as by using a bicarbonate/carbonate buffer. Such (partially) de-O-acetylated saccharides can be oxidised for activation (e.g. periodate oxidation), conjugated to a carrier (e.g. CRM197) under reducing conditions (e.g. using sodium cyanoborohydride), and then (optionally) any unreacted aldehydes in the saccharide can be capped (e.g. using sodium borohydride) [99]. Conjugation may be performed on lyophilized material e.g. after co-lyophilizing activated saccharide and carrier.

A serotype 19A saccharide may be oxidised for activation (e.g. periodate oxidation), conjugated to a carrier (e.g. CRM197) in DMSO under reducing conditions, and then (optionally) any unreacted aldehydes in the saccharide can be capped (e.g. using sodium borohydride) [103]. Conjugation may be performed on lyophilized material e.g. after co-lyophilizing activated saccharide and carrier.

Pneumococcal conjugates can ideally elicit anticapsular antibodies that bind to the relevant saccharide e.g. elicit an anti-saccharide antibody level ≥0.20 µg/mL [104]. The antibodies may be evaluated by enzyme immunoassay (EIA) and/or measurement of opsonophagocytic activity (OPA). The EIA method has been extensively validated and there is a link between antibody concentration and vaccine efficacy.

Further Antigens from Other Pathogen(s)

Compositions of the invention can include antigen(s) from further pathogen(s). The use of an aluminium hydroxyphosphate adjuvant, and avoidance of an aluminium hydroxide adjuvant, is advantageous in the context of such combinations because, as described above, the additional antigens (in particular bacterial capsular saccharides) may be sensitive to the hydroxide salt.

For example, the composition may comprise one or more of the following further antigen(s):

an antigen from hepatitis B virus, such as the surface antigen HBsAg.

an antigen from *Bordetella pertussis*, such as pertussis holotoxin (PT) and filamentous haemagglutinin (FHA) from *B. pertussis*, optionally also in combination with pertactin and/or agglutinogens 2 and 3.

a diphtheria antigen, such as a diphtheria toxoid.

a tetanus antigen, such as a tetanus toxoid.

a saccharide antigen from *Haemophilus influenzae* B (Hib), typically conjugated, inactivated poliovirus antigen(s).

Where a diphtheria antigen is included in the composition if is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Extemporaneous Preparation

The invention also provides a kit comprising: (i) a first component comprising at least one fHBP antigen adsorbed to an aluminium hydroxyphosphate adjuvant, as described above; and (ii) a second component comprising a non-meningococcal immunogen. The kit components can be mixed to give an immunogenic composition for administering to a patient to protect against multiple pathogens.

The invention also provides a method for preparing a combined vaccine, comprising a step of mixing: (i) a first component comprising at least one fHBP antigen adsorbed to an aluminium hydroxyphosphate adjuvant, as described above; and (ii) a second component comprising a non-meningococcal immunogen. The mixed material may then be administered to a patient. The second component may be lyophilised, such that an aqueous first component reconstitutes it.

Pharmaceutical Compositions

The invention is concerned with immunogenic compositions for administration to a patient. These compositions are pharmaceutical acceptable and will typically include a suitable carrier. A thorough discussion of pharmaceutically acceptable carriers is available in reference 105.

Effective dosage volumes can be routinely established, but a typical human dose of the composition has a volume of about 0.5 ml.

The pH of a composition of the invention is usually between 6 and 8, and more preferably between 6.5 and 7.5 (e.g. about 7). As already discussed above, compositions may include a buffer e.g. a Tris buffer, a citrate buffer, phosphate buffer, a succinate buffer (such as a sodium succinate buffer), or a histidine buffer.

In the first aspect of the invention, a particular pH is used prior to and/or during adsorption, as explained above, if the adsorption is stable, however, that pH does not have to be maintained after adsorption but can be allowed to rise e.g. closer to neutral. After adsorption, therefore, such a composition may be buffered at a pH above the adjuvant's PZC.

Similarly, the pH of a composition according to the second aspect should be in the range of 5.0 to 7.0 before and/or during adsorption, but may be outside this range (e.g. in the range 7.0 to 8.0) after adsorption. Ideally, though, compositions of the second aspect are maintained with a post-adsorption pH in the range of 5.0 to 7.0 by the use of a buffer.

If adsorption has taken place at a pH above the adjuvant's PZC then, if the adsorption is stable, the pH does not have to be maintained but can be allowed to drop e.g. closer to neutral. After adsorption, therefore, such a composition may be buffered at a pH below the adjuvant's PZC.

The pH of a composition according to the third aspect is within 1.2 pH units of the adjuvant's PZC before and/or during adsorption, but may be outside this range after adsorption. Ideally, though, compositions of the third aspect are maintained with a post-adsorption pH within 1.2 pH units of the adjuvant's PZC.

In some embodiments, a composition of the invention includes a buffer with a pKa between 3.5 and 6.5, particularly when used in combination with saline. This formulation is said to be useful with fHBP in reference 106. A succinate buffer with 1-10 mM succinate (e.g. 5 mM) is useful, with a pH between 5.8 and 6.0. The composition may include $MgCl_2$, KCl and/or NaCl.

The composition may be sterile and/or pyrogen-free. Compositions of the invention may be isotonic with respect to humans.

Compositions of the invention may include sodium salts (e.g. sodium chloride) to give tonicity. A concentration of 10±2 mg/ml NaCl is typical e.g. about 9 mg/ml.

Compositions of the invention for administration to patients are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fail in a relatively broad range that can be determined through routine trials. The antigen content of compositions of the invention will generally be expressed in terms of the amount of protein per dose.

Meningococci affect various areas of the body and so the compositions of the invention may be prepared in various liquid forms. For example, the compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are most typical.

Compositions of the invention may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Compositions of the invention may comprise detergent e.g. a Tween (polysorbate), such as Tween 80. Detergents are generally present at low levels e.g. <0.01%, but higher levels have been suggested for stabilising antigen formulations [106] e.g. up to 10%. An example composition may include from 0.01 to 0.05% polysorbate, and this is particularly useful when using lipidated fHBP antigen(s).

Methods of Treatment

The invention also provides a method for raising an immune response in a mammal, comprising administering a composition of the invention to the mammal. The immune response is preferably protective against meningococcus and preferably involves antibodies. The method may raise a booster response in a patient that has already been primed.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides compositions of the invention for use as a medicament. The medicament is preferably used, as described above, to raise an immune response in a mammal (i.e. it is an immunogenic composition) and is more preferably a vaccine.

The invention also provides the use of at least one fHBP antigen and an aluminium hydroxyphosphate adjuvant in the manufacture of a medicament for raising an immune response, as described above, in a mammal.

These uses and methods are preferably for the prevention and/or treatment of a disease caused by *N. meningitidis* e.g. bacterial (or, more specifically, meningococcal) meningitis, or septicemia.

One way of checking efficacy of therapeutic treatment involves monitoring meningococcal infection after administration of the composition of the invention. One way of checking efficacy of prophylactic treatment involves monitoring immune responses against antigens after administration of the composition. Immunogenicity of compositions of the invention can be determined by administering them to test subjects (e.g. children 12-16 months age, or animal models) and then determining standard parameters including serum bactericidal antibodies (SBA) and ELISA titres (GMT) for meningococcus. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Compositions of the invention will generally be administered directly to a patient. Direct delivery may be accomplished by parenteral injection (e.g. subcutaneously, intraperitoneally, intravenously. Intramuscularly, or to the interstitial space of a tissue), or by any other suitable route. The invention may be used to elicit systemic and/or mucosal immunity. Intramuscular administration to the thigh or the upper arm is preferred. Injection may be via a needle (e.g. a hypodermic needle), but needle-free injection may alternatively be used. A typical intramuscular dose is 0.5 ml.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 107-113, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

Where the invention concerns an "epitope", this epitope may be a B-cell epitope and/or a T-cell epitope, but will usually be a B-cell epitope. Such epitopes can be identified empirically (e.g. using PEPSCAN [114,115] or similar methods), or they can be predicted (e.g. using the Jameson-Wolf antigenic index [116], matrix-based approaches [117], MAPITOPE [118], TEPITOPE [119,120], neural networks [121], OptiMer & EpiMer [122,123], ADEPT [124], Tsites [125], hydrophilicity [126], antigenic index [127] or the methods disclosed in references 128-132, etc.). Epitopes are the parts of an antigen that are recognised by and bind to the antigen binding sites of antibodies or T-cell receptors, and they may also be referred to as "antigenic determinants".

Where the invention uses a "purified" antigen, this antigen is separated from its naturally occurring environment. For example, the antigen will be substantially free from other meningococcal components, other than from any other purified antigens that are present. A mixture of purified antigens will typically be prepared by purifying each antigen separately and then re-combining them, even if the two antigens are naturally present in admixture.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref, 133. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 134.

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

Aluminium Adjuvants

Adsorption of fHBP to different aluminium adjuvants under different conditions was studied. Various fHBP antigens were used, including a single fHBP (predicted pI of 7.4) or hybrid mixtures of 2 or 3 fHBPs. Some experiments included additional non-fHBP meningococcal antigens.

With an aluminium hydroxide adjuvant at pH 6.5±0.5, 100% adsorption of fHBP was seen with all single and mixed antigens. Full adsorption was also seen at slightly higher pH in the presence of 10 mM histidine buffer. The presence of additional meningococcal polypeptide adjuvants did not reduce the degree of fHBP adsorption.

In contrast, with an aluminium hydroxyphosphate adjuvant at pH 7.0 the fHBP antigen was seen to be only 50% adsorbed. This pH is below the antigen's predicted pI and above the adjuvant's PZC.

Aluminium hydroxide adjuvants generally have a PZC of about 11.4. Thus neutral pH is below the adjuvant's PZC. In contrast, neutral pH is above PZC of the aluminium hydroxyphosphate adjuvant.

Adsorption of fHBP to an aluminium hydroxyphosphate adjuvant was studied at various pH. The following data show pH and adsorption data obtained 24 hours after formulation. These three formulations have the same protein concentration (50 μg/ml) and adjuvant concentration (0.5 mg/ml), but use a 10 mM sodium phosphate buffer at different pH:

| pH | % adsorption |
|---|---|
| 7.0 | ~50% |
| 5.8 | ~95% |
| 3.5 | not adsorbed |

Thus ~95% adsorption was achieved in a pH 5.8 composition. This pH is approximately equal to the adjuvant's PZC (slightly higher) but is well below the antigen's pI. In contrast, at an increased pH (1.2 pH units higher) or decreased pH (2.3 pH units lower) adsorption was poor.

A high level of adsorption could also be achieved by increasing the amount of adjuvant 4.5-fold.

The influence of buffer and pH was studied in further experiments using 1 mg/ml adjuvant and 100 µg/ml antigen. Results were as follows:

| Buffer | pH | % adsorption |
|---|---|---|
| Sodium phosphate 10 mM | 7.1 | ~80% |
|  | 5.9 | ~95% |
|  | 5.5 | ~95% |
|  | 4 | ~80% |
| Sodium phosphate 5 mM | 6.9 | ~85% |
|  | 6.1 | ~95% |
|  | 5.9 | ~95% |
| Histidine 5 mM | 7 | ~96% |
|  | 5.9 | ~98% |
|  | 5.2 | ~95% |

Thus high adsorption (≥95%) to aluminium hydroxyphosphate could be achieved by selecting an appropriate pH. Adsorption levels above 85% were here seen only when the pH was within 1.2 pH units of the adjuvant's PZC (in the relevant buffer).

As mentioned above, these studies were performed with a fHBP having a pI of 7.4. This fHBP is referred to hereafter as fHBP-v1. Further studies were performed with fHBP from two more meningococcal strains. The predicted pI for fHBP-v2 is 5.8, and for fHBP-v3 it is 6.1. Furthermore, a fusion to combine all three of v1, v2 and v3 was studied. Each of these four proteins was formulated at 100 µg/ml with 0.222 mg/ml adjuvant and 9 mg/ml NaCl. Three different formulation pH were investigated, namely pH 5, pH 6 and pH 7. The degree of adsorption of the fHBP proteins to the aluminium hydroxyphosphate was then determined. Results were as follows:

|  |  | Adsorption at pH | | |
|---|---|---|---|---|
|  | pI | 5 | 6 | 7 |
| v1 | 7.4 | 20-40% | 90-95% | 40-60% |
| v2 | 5.8 | >95% | >95% | <25% |
| v3 | 6.1 | 90-95% | >95% | 80-85% |
| v1 + v2 + v3 | — | >95% | >95% | 85-90% |

These results confirm that the v1/v2/v3 combination, which includes one fHBP with a pI of 5.8 and another with a pI of 6.1 (i.e. both between 5.0 and 7.0), could achieve adsorption levels of ≥85% using an aluminium hydroxyphosphate adjuvant with a PZC between 5.0 and 7.0. Moreover, the highest levels of adsorption for this combination were seen when the pH was within 1.2 pH units of the adjuvant's point of zero charge (i.e. at pH 5 or pH 6, rather than at pH 7).

High adsorption was seen except (i) for v1 and v2, when the pH was more than 1.2 units higher than the adjuvant's PZC (ii) for v1, when the pH was lower than the adjuvant's PZC and the fHBP's pI was outside the range of 5.0 to 7.0. The relatively low adsorption of the v2 fHBP at pH 7 could be overcome by adding a second fHBP with a pI in the range of 5.0 to 7.0.

Thus mixtures of multiple fHBP variants with different pI values can successfully be formulated with high levels of adsorption without requiring aluminium hydroxide.

Immunostimulatory Oligonucleotide+Polycationic Polymer Adjuvant

As an alternative to using an aluminium-based adjuvants the invention can use a particulate complex of an immunostimulatory oligonucleotide and a polycationic polymer, such as IC31.

The three polypeptides which make up the '5CVMB' vaccine disclosed in reference 12 (see also ref. 135) were adjuvanted with aluminium hydroxide and/or IC31. One of these three polypeptides includes a fHBP antigen.

In a first set of experiments, nine groups of mice received 10 µg of antigens, 3 mg/ml of aluminium hydroxide and varying doses of IC31. Groups received the following nine compositions, with groups 7-9 receiving the same antigens as 1-6 but differently formulated:

| | Antigen dose (µg) | IC31 volume* (µl) | Al—H (mg/ml) |
|---|---|---|---|
| 5 | 10 | 0 | 3 |
| 6 | 10 | 100 | 0 |
| 7 | 10 | 0 | 3 |
| 9 | 10 | 100 | 0 |

*A standard IC31 suspension was used. 100 µl of this suspension gave full-strength. Lower volumes gave lower strengths. To preserve the volume for the lower-strength compositions, buffer was added up to 100 µl.

Sera from the mice were tested against a panel of meningococcal strains for bactericidal activity.

Bactericidal titers from experiment MP03 were as follows against six different strains, A to F:

| | A | B | C | D | E | F |
|---|---|---|---|---|---|---|
| 5 | >65536 | 2048 | 4096 | 8192 | 256 | 32768 |
| 6 | >65536 | 4096 | >8192 | 8192 | 1024 | >65536 |
| 7 | >65536 | 2048 | 4096 | 4096 | 256 | 4096 |
| 9 | 32768 | 8192 | >8192 | >8192 | 4096 | >65536 |

Thus the titers obtained with IC31 were usually better than those obtained with Al-H.

The '5CVMB' vaccine was combined with a tetravalent mixture of meningococcal conjugates against serogroups A, C, W135 and Y. The mixture was adjuvanted with Al-H or IC31 (at high or low concentration). Bactericidal titers were as follows against a panel with one strain from each of serogroups A, C, W135 and Y:

| | A | C | W135 | Y |
|---|---|---|---|---|
| Un-immunised | <16 | <16 | <16 | <16 |
| No adjuvant | 1024 | 256 | 128 | 512 |
| IC31$^{high}$ | 32768 | 16384 | 4096 | 4096 |
| IC31$^{low}$ | 16384 | 8192 | 1024 | 2048 |
| Al-hydroxide | 16384 | 8192 | 1024 | 4096 |

Thus the best titers were seen with IC31.

In separate experiments a triple-fusion polypeptide containing three variants of fHBP, in the order II-III-I (as disclosed in reference 27), was adjuvanted with aluminium hydroxide or IC31.

In a first set of experiments, six groups of mice received 20 µg of antigen (with or without a purification tag), 3 mg/ml of aluminium hydroxide and 100 µl of IC31. Groups received the following:

| | Antigen dose (µg) | Antigen tag | IC31 volume (µl) | Al—H (mg/ml) |
|---|---|---|---|---|
| 1 | 20 | No | 100 | 0 |
| 2 | 20 | Yes | 100 | 0 |
| 5 | 20 | No | 0 | 3 |
| 6 | 20 | Yes | 0 | 3 |

Sera from the mice were tested against a panel of meningococcal strains for bactericidal activity.

Sera from experiment MP05 were again tested against a panel of strains (25 in total). 56% of strains in group 1 (IC31, no tag) had a titer ≥1:1024 vs. only 36% of strains in group 5 (A1-H, no tag). Similarly, 76% of strains in group 1 had a titer ≥1:128 while this titer was observed in only 64% of strains in group 5. Looking at the untagged antigens, 84% of strains in group 2 (IC31) had a titer ≥1:128 vs. 76% in group 6 (A1-H). Thus higher bactericidal titers were achieved using IC31.

Further immunogenicity experiments used the fHBP$_{II-III-I}$ antigen in combination with the NadA and 287-953 antigens in experiment MP04, with the same groupings and strain panel. Group 1 showed a bactericidal titer ≥1:128 in 100% of strains, compared to only 84% in group 5, With a more stringent threshold of ≥1:1024, sera from group 1 were bactericidal against 88% of strains, compared to only 56% in group 5. Similar results were observed with tagged antigens, where 88% of group 2 had a bactericidal titer of ≥1:128 compared to 80% in group 6. Again, therefore, better anti-meningococcus immune responses were obtained with IC31.

In similar experiments the combination of fHBP$_{II-III-I}$, NadA and 287-953 was adjuvanted with A1-H or IC31. These compositions were compared with a composition comprising the 5CVMB vaccine including outer membrane vesicles, adjuvanted with Al—H. The IC31-adjuvanated vaccine provided a higher % coverage across 12 tested strains than any other composition.

Thus IC31 is an effective adjuvant for fHBP.

It will be understood that the invention has been described by way of example only and modifications may be made whilst remaining within the scope and spirit of the invention.

REFERENCES

[1] Masignani et al. (2003) *J Exp Med* 197:789-799.
[2] Welsch et al. (2004) *J Immunol* 172:5605-15.
[3] Hou et al. (2005) *J Infect Dis* 192(4):580-90.
[4] WO03/063766.
[5] Fletcher et al. (2004) *Infect Immun* 72:2088-2100.
[6] Zhu et al. (2005) *Infect Immun* 73(10):6838-45.
[7] Cantini et al. (2006) *J. Biol. Chem.* 281:7220-7227
[8] WO2004/048404
[9] WO03/020756.
[10] Sturgess et al. (1999) *Vaccine* 17:1169-1178.
[11] U.S. Pat. No. 7,404,960.
[12] Giuliani et al. (2006) *PNAS USA* 103:10834-9.
[13] Hem & HogenEsch (2007) Chapter 4 of *Vaccine Adjuvants and Delivery Systems* (ed. Singh).
[14] Burrell et al. (2001) *Vaccine* 19:275-81.
[15] *Methods in Moelcular Medicine*, Vol. 42 (ed. O'Hagan) Vaccine Adjuvants . . . .
[16] WO01/22992.
[17] Bjellqvist et al. (1993) *Electrophoresis* 14:1023-31.
[18] Gasteiger et al. (2005) *Protein Identification and Analysis Tools on the ExPASy Server* in *The Proteomics Protocols Handbook* (ed. John M. Walker), Humana Press (2005).
[19] Krieg (2003) *Nature Medicine* 9:831-835.
[20] McCluskie et al. (2002) *FEMS Immunology and Medical Microbiology* 32:179-185.
[21] WO98/40100.
[22] U.S. Pat. No. 6,207,646.
[23] U.S. Pat. No. 6,239,116.
[24] U.S. Pat. No. 6,429,199.
[25] Schellack et al. (2006) *Vaccine* 24:5461-72.
[26] Lingnau et al. (2007) *Expert Rev Vaccines* 6:741-6.
[27] WO2004/084938.
[28] Kamath et al. (2008) *Eur J Immunol* 38:1247-56.
[29] Riedl et al. (2008) *Vaccine* 26:3461-8.
[30] Kritsch et al. (2005) *J Chromatography B* 822:263-70.
[31] Lingnau et al. (2003) *Vaccine* 20:3498-508.
[32] Tettelin et al. (2000) *Science* 287:1809-1815.
[33] WO00/66741.
[34] WO99/57280
[35] Martin et al. (1997) *J Exp Med* 185(7):1173-83.
[36] WO96/29412.
[37] U.S. Pat. No. 5,698,438.
[38] Perkins-Balding et al. (2003) *Microbiology* 149:3423-35.
[39] WO01/55182.
[40] WO01/38350.
[41] WO00/23595.
[42] Ram et al. (2003) *J Biol Chem* 278:50853-62.
[43] WO2004/014417.
[44] WO98/53851
[45] U.S. Pat. No. 6,531,131
[46] WO00/26384.
[47] U.S. Pat. No. 6,645,503
[48] WO03/070282.
[49] WO94/08021
[50] WO2004/015099.
[51] WO2007/144316.
[52] WO2007/144317.
[53] WO03/080678.
[54] Glode et al. (1979) *J Infect Dis* 139:52-56
[55] WO94/05325; U.S. Pat. No. 5,425,946.
[56] Arakere & Frasch (1991) *Infect. Immun.* 59:4349-4356.
[57] Michon et al. (2000) *Dev. Biol* 103:151-160.
[58] Rubinstein & Stein (1998) *J. Immunol.* 141:4357-4362.
[59] WO2005/033148
[60] WO2007/000314.
[61] *Research Disclosure*, 453077 (January 2002)
[62] EP-A-0378881.
[63] EP-A-0427347.
[64] WO93/17712
[65] WO94/03208.
[66] WO98/58668.
[67] EP-A-0471177.
[68] WO91/01146
[69] Falugi et al. (2001) *Eur J Immunol* 31:3816-3824.
[70] Baraldo et al. (2004) *Infect Immun* 72(8):4884-7.
[71] EP-A-0594610.
[72] Ruan et al. (1990) *J Immunol* 145:3379-3384.
[73] WO00/56360.
[74] Kuq et al. (1995) *Infect Immun* 63:2706-13.
[75] Michon et al. (1998) *Vaccine*. 16:1732-41.
[76] WO02/091998.
[77] WO01/72337
[78] WO00/61761.
[79] WO00/33882
[80] WO2007/000341.
[81] Bethel G. S. et al., *J. Biol. Chem.*, 1979, 254, 2572-4
[82] Hearn M. T. W., *J. Chromatogr.*, 1981, 218, 509-18
[83] WO2007/000343.
[84] *Mol. Immunol.*, 1985, 22, 907-919
[85] EP-A-0208375
[86] WO00/10599
[87] Gever et al., Med. Microbiol. Immunol, 165:171-288 (1979).
[88] U.S. Pat. No. 4,057,685.
[89] U.S. Pat. Nos. 4,673,574; 4,761,283; 4,808,700.

[90] U.S. Pat. No. 4,459,286.
[91] U.S. Pat. No. 5,204,098
[92] U.S. Pat. No. 4,965,338
[93] U.S. Pat. No. 4,663,160.
[94] WO2007/000342.
[95] *WHO Technical Report Series* No. 927, 2005. Pages 64-98.
[96] US-2008/0102498.
[97] US-2006/0228381.
[98] US-2007/0231340.
[99] US-2007/0184072.
[100] US-2006/0228380.
[101] WO2008/143709.
[102] WO2007/071707
[103] US-2007/0184071.
[104] Jodar et al. (2003) *Vaccine* 21:3265-72.
[105] Gennaro (2000) *Remington: The Science and Practice of Pharmacy.* 20th edition, ISBN: 0683306472.
[106] WO2007/127665.
[107] *Methods In Enzymology* (S. Colowick and N. Kaplan, eds., Academic Press, Inc.)
[108] *Handbook of Experimental Immunology*, Vols. I-IV (D. M. Weir and C. C. Blackwell, eds, 1986, Blackwell Scientific Publications)
[109] Sambrook et al. (2001) *Molecular Cloning: A Laboratory Manual,* 3rd edition (Cold Spring Harbor Laboratory Press).
[110] *Handbook of Surface and Colloidal Chemistry* (Birdi, K. S. ed., CRC Press, 1997)
[111] Ausubel et al. (eds) (2002) *Short protocols in molecular biology,* 5th edition (Current Protocols).
[112] *Molecular Biology Techniques: An Intensive Laboratory Course,* (Ream et al., eds., 1998, Academic Press)
[113] *PCR (Introduction to Biotechniques Series),* 2nd ed. (Newton & Graham eds., 1997, Springer Verlag)
[114] Geysen et al. (1984) *PNAS USA* 81:3998-4002.
[115] Carter (1994) *Methods Mol Biol* 36:207-23.
[116] Jameson, B A et al. 1988, *CABIOS* 4(1):181-186.
[117] Raddrizzani & Hammer (2000) *Brief Bioinform* 1(2): 179-89.
[118] Bublil et al. (2007) *Proteins* 68(1):294-304.
[119] De Lalla et al. (1999) *J. Immunol.* 163:1725-29.
[120] Kwoke et al. (2001) *Trends Immunol* 22:583-88.
[121] Brusic et al. (1998) *Bioinformatics* 14(2):121-30
[122] Meister et al. (1995) *Vaccine* 13(6):581-91.
[123] Roberts et al. (1996) *AIDS Res Hum Retroviruses* 12(7):593-610.
[124] Maksyutov & Zagrebelnaya (1993) *Comput Appl Biosci* 9(3):291-7.
[125] Feller & de la Cruz (1991) *Nature* 349(6311):720-1.
[126] Hopp (1993) *Peptide Research* 6:183-190.
[127] Welling et al. (1985) *FEBS Lett.* 188:215-218.
[128] Davenport et al. (1995) *Immunogenetics* 42:392-297.
[129] Tsurui & Takahashi (2007) *J Pharmacol Sci.* 105(4): 299-316.
[130] Tong et al. (2007) *Brief Bioinform.* 8(2):96-108.
[131] Schirle et al. (2001) *J Immunol Methods.* 257(1-2):1-16.
[132] Chen et al. (2007) *Amino Acids* 33(3):423-8.
[133] *Current Protocols in Molecular Biology* (F. M. Ausubel et al., eds., 1987) Supplement 30
[134] Smith & Waterman (1981) *Adv. Appl. Math.* 2:482-489.
[135] WO2004/032958.

What is claimed:

1. A method for raising an immune response in a human comprising administering to the human a buffered immunogenic composition comprising at least two different meningococcal fHBP antigens, both of which are at least 85% adsorbed to aluminium hydroxyphosphate adjuvant, wherein (i) each meningococcal fHBP antigen has an isoelectric point which is greater than the adjuvant's point of zero charge and (ii) the composition has a pH which is within 1.2 pH units of the adjuvant's point of zero charge.

2. The method of claim 1, wherein (i) each of the two different fHBP antigens has an isoelectric point between 5.0 and 7.0, and (ii) the aluminium hydroxyphosphate adjuvant has a point of zero charge between 5.0 and 7.0.

3. The method of claim 2, wherein the pH of the buffered composition is in the range of 5.0 to 7.0.

4. The method of claim 1, wherein (i) both of the meningococcal fHBP antigens have an isoelectric point between 5.0 and 6.0 and (ii) the aluminium hydroxyphosphate has an isoelectric point between 5.0 and 6.0.

5. The method of claim 4, wherein the immunogenic composition includes a buffer to maintain pH in the range of 5.0 to 7.0.

6. The method of claim 5, wherein the immunogenic composition includes a buffer to maintain pH in the range of 5.0 to 6.0.

7. The method of claim 1, wherein the buffered immunogenic composition is a priming aqueous suspension composition comprising two different meningococcal factor H binding protein (fHBP) antigens, both of which are adsorbed to aluminium hydroxyphosphate adjuvant, wherein both of the meningococcal fHBP antigens have an isoelectric point between 5.0 and 7.0, wherein the two different meningococcal fHBP antigens are: (a) a first polypeptide comprising an amino acid sequence having at least 99% sequence identity to SEQ ID NO: 4; and (b) a second polypeptide comprising an amino acid sequence having at least 99% sequence identity to SEQ ID NO: 6, and wherein the priming aqueous suspension composition: (i) includes a histidine buffer to maintain a pH in the range of 5.0 to 7.0; (ii) has an $Al^{+++}$ concentration <1 mg/ml; (iii) includes polysorbate 80; and (iv) includes between 1 and 500 µg/dose of each fHbp polypeptide.

8. The method of claim 7, wherein the administration is by intramuscular injection.

9. The method of claim 8, wherein the intramuscular administration is to the upper arm.

10. The method of claim 7, wherein the first polypeptide comprises the amino acid sequence of SEQ ID NO: 4 and the second polypeptide comprises the amino acid sequence of SEQ ID NO: 6.

11. The method of claim 7, wherein the priming aqueous suspension composition has a volume of about 0.5 ml.

12. The method of claim 7, wherein the priming aqueous suspension composition includes about 60 µg/dose of each fHbp polypeptide.

13. The method of claim 7, wherein the histidine is at 10 mM concentration.

14. The method of claim 7, further comprising administering to the human a second aqueous suspension composition comprising two different meningococcal factor H binding protein (fHBP) antigens, both of which are adsorbed to aluminium hydroxyphosphate adjuvant, wherein both of the meningococcal fHBP antigens have an isoelectric point between 5.0 and 7.0, wherein the two different meningococcal fHBP antigens are: (a) a first polypeptide comprising an amino acid sequence having at least 99% sequence identity to SEQ ID NO: 4; and (b) a second polypeptide comprising an amino acid sequence having at least 99% sequence identity to SEQ ID NO: 6, and wherein the second aqueous suspension composition: (i) includes a histidine buffer to maintain a pH in the range of 5.0 to 7.0; (ii) has an $Al^{+++}$ concentration <1 mg/ml; (iii) includes polysorbate 80; and (iv) includes between 1and 500 µg/dose of each fHbp polypeptide, wherein the boosting dose is administered between 4 and 16 weeks after administration of the priming aqueous suspension composition.

15. The method of claim 1, wherein the two different fHBP antigens are: (i) a first and second polypeptide; (ii) a first and third polypeptide; or (iii) a second and third polypeptide, selected from: (a) a first polypeptide comprising an amino acid sequence (i) having at least 84% sequence identity to SEQ ID NO: 1 and/or (ii) consisting of a fragment of at least 20 contiguous amino acids from SEQ ID NO: 1; (b) a second polypeptide, comprising an amino acid sequence (i) having at least 84% sequence identity to SEQ ID NO: 2 and/or (ii) consisting of a fragment of at least 20 contiguous amino acids from SEQ ID NO: 2; (c) a third polypeptide, comprising an amino acid sequence (i) having at least 84% sequence identity to SEQ ID NO: 3 and/or (ii) consisting of a fragment of at least 20 contiguous amino acids from SEQ ID NO: 3.

16. The method of claim 1, wherein the fHBP polypeptides are lipidated at a N-terminus cysteine, wherein the lipid comprises palmitoyl.

17. The method of claim 1, wherein the aluminium hydroxyphosphate has a PZC between 5.4 and 6.2.

18. The method of claim 1, wherein the aluminium hydroxyphosphate has a P/Al molar ratio between 0.85 and 1.0.

19. The method of claim 1, wherein the aluminium hydroxyphosphate is amorphous and particulate comprising plates with diameters 10-100 nm.

20. The method of claim 1, wherein the $Al^{+++}$ concentration is <2 mg/ml.

* * * * *